(12) United States Patent
Lapidus

(10) Patent No.: US 6,638,881 B2
(45) Date of Patent: Oct. 28, 2003

(54) DENTAL ADHESIVE DEVICE AND METHOD OF PRODUCING SAME

(75) Inventor: Herbert Lapidus, Ridgefield, CT (US)

(73) Assignee: Combe Incorporated, White Plains, NY (US)

(*) Notice: Subject to any disclaimer, the term of this patent is extended or adjusted under 35 U.S.C. 154(b) by 255 days.

(21) Appl. No.: 09/747,805

(22) Filed: Dec. 22, 2000

(65) Prior Publication Data
US 2002/0006980 A1 Jan. 17, 2002

Related U.S. Application Data
(60) Provisional application No. 60/171,592, filed on Dec. 23, 1999.

(51) Int. Cl.⁷ ............................................. B32B 27/12
(52) U.S. Cl. .................. 442/149; 442/151; 442/393; 442/394; 428/343; 156/278; 156/283
(58) Field of Search ................... 428/343; 442/394, 442/393, 149, 151; 156/278, 283

(56) References Cited

U.S. PATENT DOCUMENTS

| | | | |
|---|---|---|---|
| 2,897,593 A | 8/1959 | Hollander et al. | 32/2 |
| 2,978,812 A | 4/1961 | Rosenthal et al. | 32/2 |
| 3,575,915 A | 4/1971 | Novak et al. | 260/29.6 |
| 3,868,340 A | 2/1975 | Keegan et al. | 260/17.4 |
| 3,990,149 A | 11/1976 | Nedwig | 32/2 |
| 4,503,116 A | 3/1985 | Lapidus | 428/286 |
| 4,608,088 A | 8/1986 | Lokken | 106/35 |
| 4,632,880 A | 12/1986 | Lapidus | 428/523 |
| RE33,093 E | 10/1989 | Schiraldi et al. | 424/676 |
| 4,880,702 A | 11/1989 | Homan et al. | 428/354 |
| 5,166,233 A | 11/1992 | Kuroya et al. | 524/37 |
| 5,209,777 A | 5/1993 | Altwirth | 106/35 |
| 5,369,145 A | 11/1994 | Gasman et al. | 523/120 |
| 5,525,652 A | 6/1996 | Clarke et al. | 524/37 |
| 5,624,745 A | 4/1997 | Lapidus | 428/308.8 |
| 5,658,586 A | 8/1997 | Rajaiah et al. | 424/435 |

FOREIGN PATENT DOCUMENTS

| | | |
|---|---|---|
| EP | 0353375 | 8/1988 |
| EP | 0396411 | 11/1990 |
| JP | 63 54318 | 3/1988 |
| JP | 149110 | 5/1992 |
| JP | 65210 | 3/1993 |
| JP | 65211 | 3/1993 |

Primary Examiner—Elizabeth M. Cole
(74) Attorney, Agent, or Firm—Fitzpatrick, Cella, Harper & Scinto

(57) ABSTRACT

An improved dental adhesive device to hold prosthetic devices in the human mouth is made as a laminate of webs which are bonded together by deforming a film of thermoplastic ethylene oxide polymer and having an external adhesive coating on the laminate. The dental adhesive is produced by continuously applying thermoplastic ethylene oxide polymer between moving webs of cellulose acetate fibers, applying additional thermoplastic ethylene oxide polymer to the external surface of the webs, and then passing said webs in superimposed relationship between a pair of dry heated calender rolls for thermoplastically bonding said webs into a unitary structure. A dry water-activated adhesive material, such as sodium alginate, may be employed with the thermoplastic ethylene oxide polymer by being dissolved or dispersed in the polymer. Synthetic fibers are applied to the webs so as to extend transversely through the webs.

22 Claims, 7 Drawing Sheets

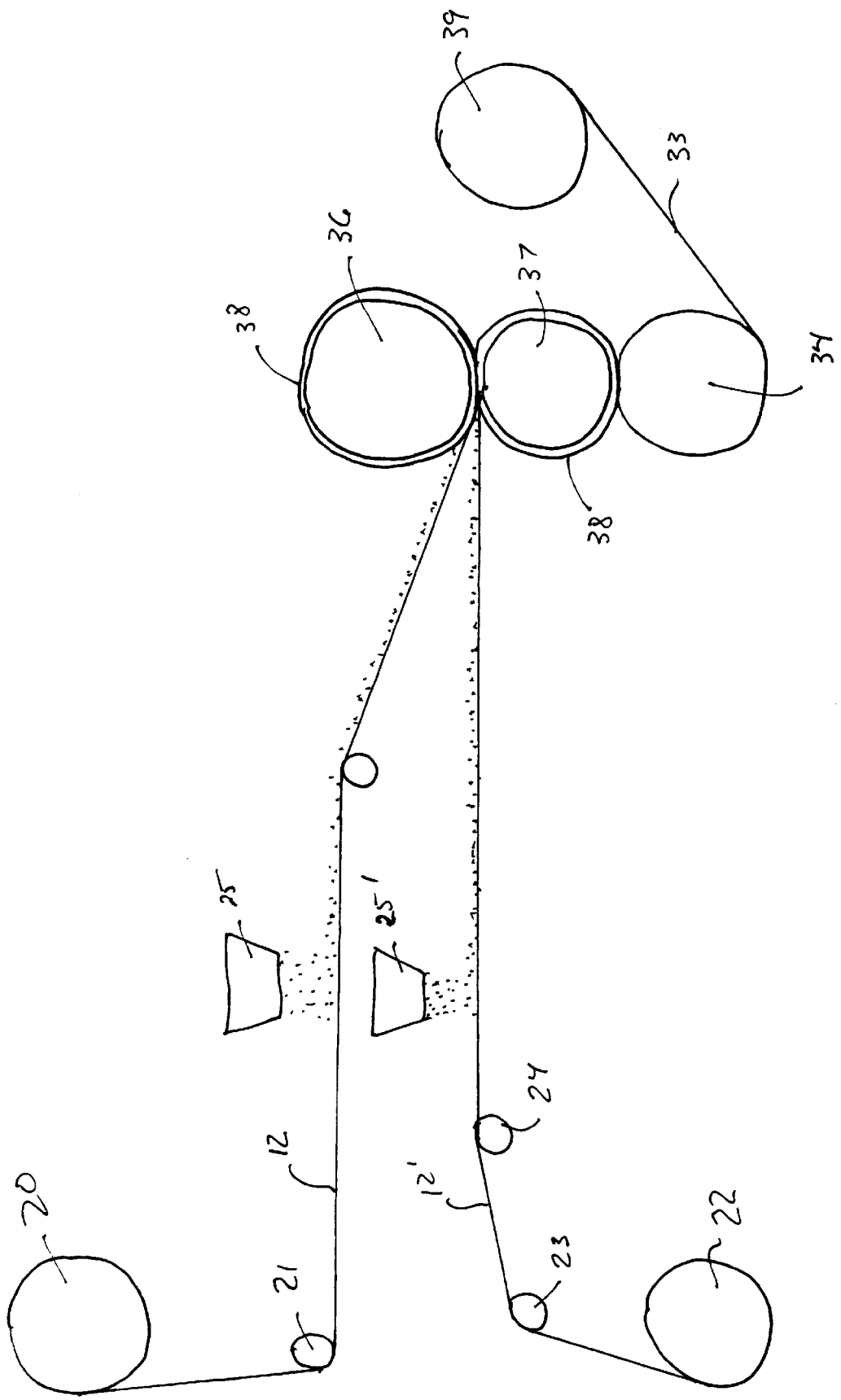

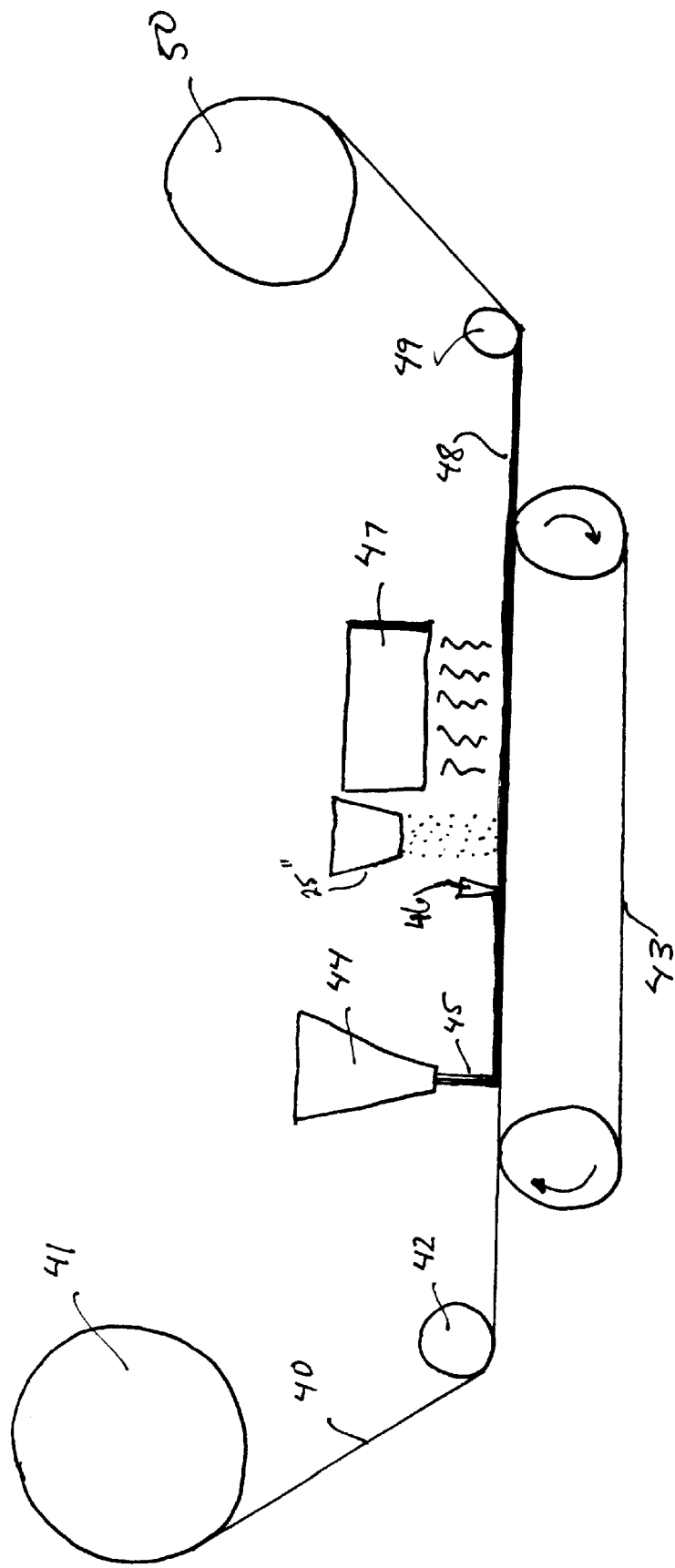

DENTAL ADHESIVE DEVICE AND METHOD OF PRODUCING SAME

This application claims the benefit of parent U.S. application Ser. No. 60/171,592, filed Dec. 23, 1999, the contents of which are hereby incorporated in their entirety into this specification.

BACKGROUND OF THE INVENTION

1. Field of the Invention

The present invention relates to an improved device for fixing in place a prosthetic device in the human mouth and a method for producing the same.

2. Description of Related Art

A superior dental adhesive product has been commercially available under the trademark SEA-BOND® and is used in the human mouth to bond a denture to the soft gum tissues. As described in U.S. Pat. No. 4,503,116, the disclosure of which is incorporated herein by reference, the dental adhesive is a laminate of webs having a carrier portion with fibers thermoplastically bonded together by an interposed layer of ethylene oxide polymer powder. The ethylene oxide polymer powder is a dry, water-activated adhesive.

Accordingly, the thermoplastic properties of the ethylene oxide polymer make a better laminate and its water-activated adhesive properties improve the laminate denture fixability. Such fixative properties are further improved by admixing another dry, water-activated adhesive material, such as sodium alginate, with the ethylene oxide polymer powder to promote formation of a gel-like adhesive mass between the denture plate and the mouth tissue.

The dental adhesive product disclosed in U.S. Pat. No. 4,503,116 contains a fiber-faced web which is formed by arranging a layer of loose synthetic fibers on a carrier such as a cellulosic paper. The loose fibers are passed through the carrier by needle-punching them so the fibers protrude from either side of the paper. A pair of such fiber-faced carriers are heat- and pressure-bonded together by the thermoplastic powder layer, such as ethylene oxide polymer powder to which a dry powder fixative, such as sodium alginate, has been added.

A thin version of this dental adhesive is disclosed in U.S. Pat. No. 4,632,080, the disclosure of which is also incorporated by reference into this disclosure. This thin version comprises web laminates of thin edible papers.

U.S. Pat. No. 5,624,745, the disclosure of which is also incorporated by reference, describes a further improved laminate dental adhesive in which ethylene oxide polymer is applied as a pre-cast film, not as a powder.

Finally, U.S. Pat. No. 5,658,586 discloses a denture adhesive composition comprising one or more water soluble adhesive components and at least one non-adhesive self-supporting layer. The patent discloses that the denture adhesive composition can also comprise a coating on one side that is sticky to dry dentures.

While some of the resulting products have enjoyed great commercial success, further improvements are desired.

In particular, as described above the adhesive component of the prior art laminates is sandwiched between two fibrous material scrim. The adhesive is activated by moisture and diffuses through the scrim to form a sticky coating on the outside of the laminate. The holding power of the dental adhesive product is therefore somewhat limited by the ability of activated adhesive to form on the exterior surface of the laminate and establish a bond between the denture and the oral cavity.

It is therefore desirable to improve the adhesive action of the laminate product to provide a stronger bond between the denture and oral cavity and to make the adhesive mixture on the exterior surface of the scrim immediately available without the need for diffusion through the layers.

SUMMARY OF THE INVENTION

Accordingly, it is an object of the present invention to provide a dental adhesive product having an improved adhesive action to form stronger and more lasting bonds between the denture and the oral cavity.

It is another object to provide an improved dental adhesive product which is readily manufactured.

These and other objects and advantages are obtained by the dental adhesive product and methods of this invention.

Thus, the invention provides a dental adhesive product comprising a laminate of a pair of superimposed fiber-faced webs, each web having an external and an internal surface with fibers held therein and protruding therefrom to present a fiber facing on each surface of each of said webs, a first ethylene oxide polymer composition sandwiched between said internal surfaces of said webs, and a second ethylene oxide polymer composition dispersed on said external surface of at least one of said webs.

The invention also provides method for producing a dental adhesive product comprising:

a) applying a first thermoplastic ethylene oxide polymer composition to a surface of a first fibrous web;

b) contacting the first web with a second fibrous web in superimposed relation to form a composition whereby said first ethylene oxide polymer composition is arrayed between and contacts said first and second webs;

c) applying a second thermoplastic ethylene oxide polymer composition to at least one surface of the first or second webs opposite to the surface contacting the first ethylene oxide polymer composition; and d) forming a unitary laminate of said first and second ethylene oxide polymer compositions and said first and second webs.

The invention further provides a method for producing a dental adhesive product comprising:

a) applying a first thermoplastic ethylene oxide polymer composition to a surface of a first fibrous web;

b) contacting the first web with a second fibrous web in superimposed relation to form a composition whereby said first ethylene oxide polymer composition is arrayed between and contacts said first and second webs;

c) forming a first unitary laminate of said first ethylene oxide polymer composition and said first and second webs;

d) applying a second thermoplastic ethylene oxide polymer composition to at least one surface of said first unitary laminate; and e) forming a second unitary laminate from said second ethylene oxide polymer composition and said first unitary laminate.

In one aspect a dental adhesive product is obtained by applying an external coating comprising at least a thermoplastic ethylene oxide polymer to at least one surface of a fibrous web of a denture adhesive product. Heat and pressure are thereafter applied, inter alia, to deform the ethylene oxide polymer coating and thereby thermoplastically bond the external coating to the web(s) as a unitary structure.

The external coating of ethylene oxide polymer can be applied as a powder to a pre-existing dental adhesive product prepared as described above and then bonded thereto to form the improved product. Alternatively, and as more fully described herein, the external coat can be applied to a scrim surface prior to thermoplastically bonding a pair of webs with an interposed layer of dental adhesive. After lamination, the resulting assembly is a dental adhesive laminated product which has improved mechanical properties and which forms a more durable, stronger seal between the gum and denture plate.

While ethylene oxide has been known as a water-activated adhesive, the invention contemplates advantageously using its thermoplastic and film-forming properties in an external coating to make a better laminate and to improve the laminate's denture fixative abilities. Moreover, such fixative properties may be further improved by employing additional water-activated adhesive material in the ethylene oxide polymer matrix present in the external coat or on the internal sandwiched layer or by dispersing additives such as gums, and the like, in the polymer matrix. Such embodiments further promote the formation of a gel-like adhesive mass between the denture plate and the mouth tissue.

It is also contemplated that synthetic fibers can be punched transversely through the webs. The free, internal ends of the fibers are commingled by entangling and mechanically interlocking the free ends of the fibers. Such a step may be employed just before the superimposed webs pass between heated calender rolls. Accordingly, even greater bonding between the webs is achieved by the interlocked fibers.

The invention may be more completely understood by the following detailed description and the drawings of the preferred embodiment referred to therein.

BRIEF DESCRIPTION OF THE DRAWINGS

In the accompanying drawings.

DESCRIPTION OF THE PREFERRED EMBODIMENTS

Figure 1:
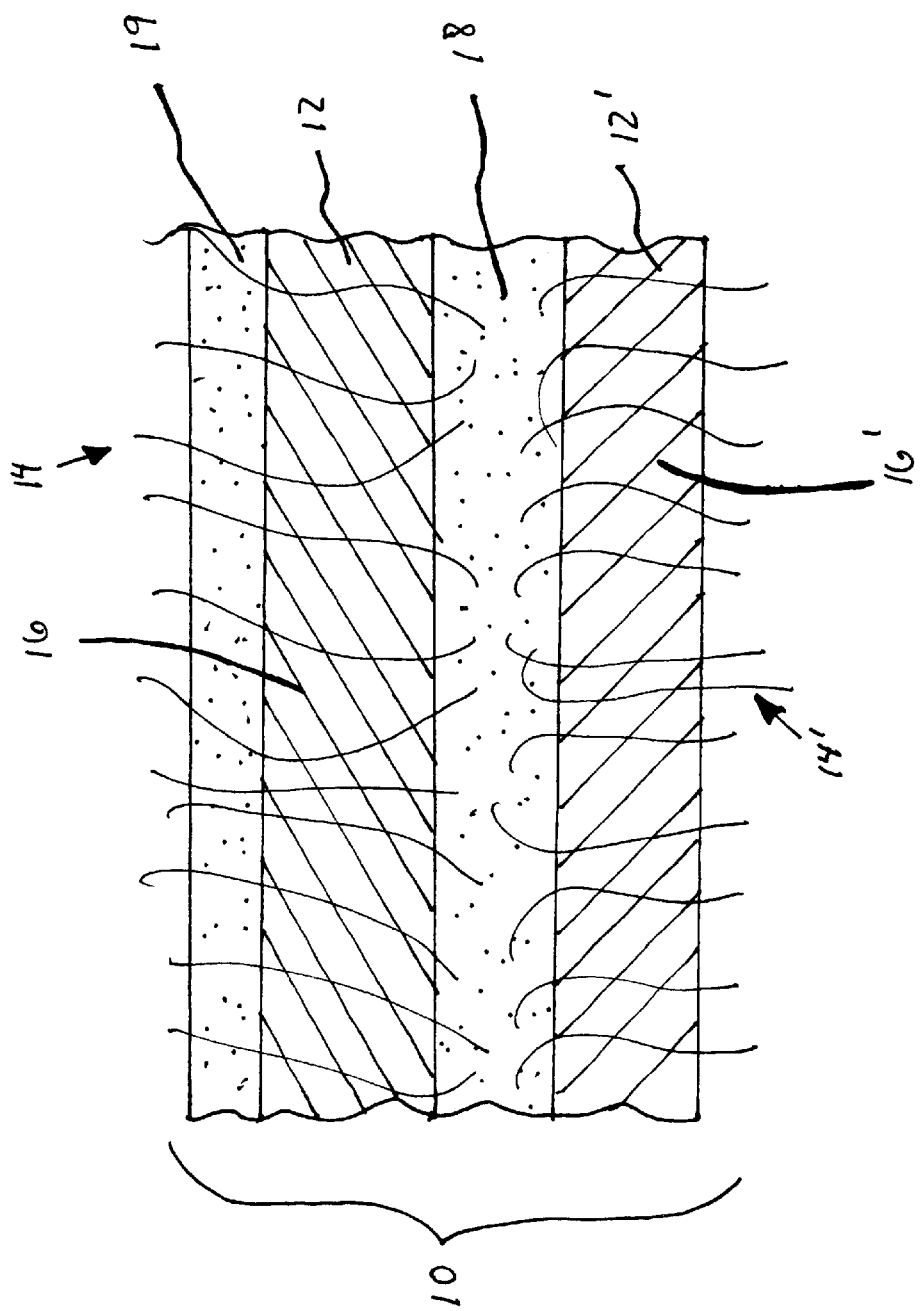
FIG. 1 is an enlarged cross-sectional view of the improved adhesive device comprising two fiber-face webs with a layer of water-activated adhesive therebetween and an additional layer of water-activated adhesive thereon.

In FIG. 1 there is illustrated a laminated adhesive device 10. Fiber-faced webs 12, 12' are formed by, for example, needle punching loose synthetic fibers 14, 14' through elongated sheets of cellulosic paper 16, 16' as a carrier. Preferably the fibers 14, 14' are made from a microcellulose material such as cellulose acetate. Paper carrier 16 can be made from cellulose and regenerated cellulose as well as polypropylene as set forth in U.S. Pat. No. 4,503,116, the disclosure of which is hereby incorporated by reference. The fiber-faced webs sandwich a thermoplastic adhesive 18; and an external layer of adhesive 19 is present on at least one free surface of the carrier.

Adhesives 18 and 19 may be the same or different. They may be any of many well-known adhesives, and preferably comprise up to approximately 90% by weight of the ethylene oxide polymer/water-activated adhesive mixture. The balance of the adhesive typically comprises sodium alginate, which has been used as the water-activated adhesive with much success. KELVIS® brand sodium alginate is particularly preferred. Additionally, materials such as cellulose gum, sodium carboxymethyl cellulose, methyl cellulose, polyvinyl methyl ether maleate, gelatin, pectin, karaya gum and tragacanth gum, among others, can each be used as the adhesive in combination with the sodium alginate or in its stead. Of course, any suitable combination of the adhesives may also be used.

The ethylene-oxide polymer otherwise known as polyoxyethylene oxide can be employed in various molecular weights. Typically, ethylene oxide polymer such as polyox WSR-301, WSR-205, WSR-1105, and mixtures thereof can be employed. A preferred film is formed from a 50:50 weight blend of KELVIS® sodium alginate and polyox WSR-301 ethylene oxide polymer. The amount of the alginate/polyox film on the web is preferably controlled at 1.5 ounces of the polymers per square yard of the web.

Useful adhesive mixtures include 15% by weight ethylene oxide polymer, 65% by weight polyvinyl methyl ether maleate and 20% by weight pectin. In addition, 65% by weight ethylene oxide, 15% sodium alginate and 20% methyl cellulose forms a desired adhesive.

Dry water-activated adhesives are also advantageously employed in conjunction with the ethylene oxide polymer. These adhesives can be admixed with ethylene oxide polymer powder to form either the internal bonding material or the external adhesive layer.

It should be appreciated that the fiber-faced web formed of the carrier and fibers need not be unwoven needle-punched web. The invention also envisions use of other materials such as simple non-woven webs or even woven napped materials. Additionally, the web material while advantageously using cellulose or cellulose acetate, may also be produced from polypropylene, nylon, other suitable materials or appropriate combinations of the aforementioned.

Figure 2:
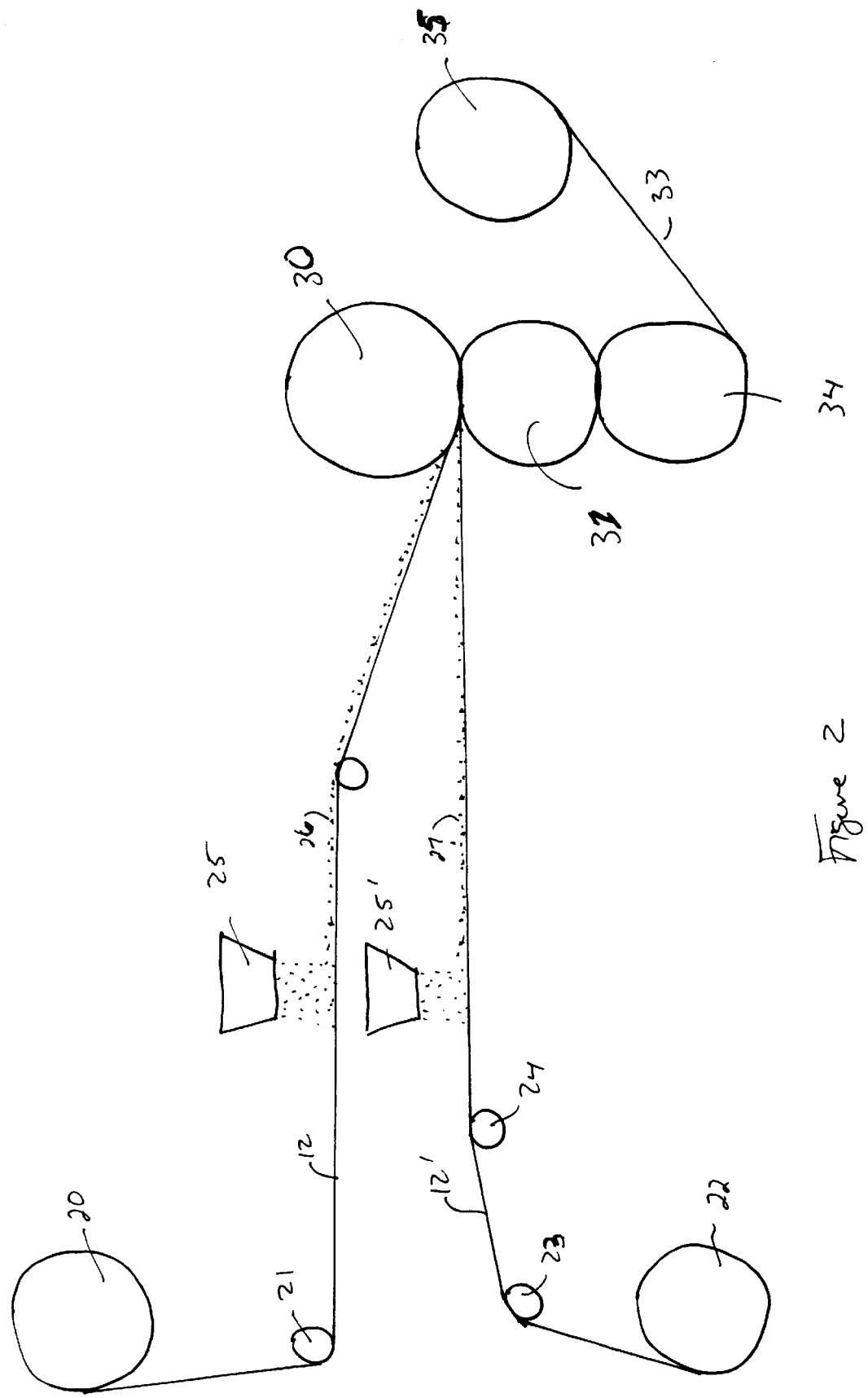
FIG. 2 is a schematic side view of the production equipment for conducting the improved method of the invention to produce the improved dental adhesive product.

By referring to FIG. 2 the process for making the product according to the invention may be more readily understood. Prior to the conducting of the hereinafter described method, fiber-faced webs 12, 12' have been put up as a roll of material for use in the process. The upper web 12 is fed from a roll 20 under an idler roll 21. Web 12' is fed from roll 22 over idler roll 23 horizontally over guide roll 24.

The internal and external adhesive materials are applied to webs 12, 12' from powder spreaders 25 and 25', respectively. Powder spreader 25 is utilized to deposit an ethylene oxide polymer-containing powder layer 26 on web 12 and powder spreader 25' deposits an ethylene oxide polymer powder-containing layer 27 on web 12'.

The upper web 12 containing powder layer 26 is superimposed above and in contact with web 12' containing powder layer 27 so that the powder adhesive 27 is sandwiched therebetween. The superimposed webs are then fed to a nip between heated calender rolls 30, 31 to fuse the webs and adhesive layers into a unitary laminate.

Thereafter, the laminated product is conducted through the nip between calender roll 31 and guide roll 34 and collected as a continuous coiled product on roll 35.

When passed between calandar rolls 30, 31, the ethylene polymer film in both the internal and external layers partially melts and deforms to bond the fibers 14, 14' and carriers 16, 16' forming the webs into an integral structure. No liquid is required to form the product, other than that which is incidently present in the web or in the ethylene oxide polymer. The temperature of the heated calender rolls 30, 31 is preferably sufficient to melt the ethylene oxide polymer, but low enough not to affect the web or soften the water-activated adhesives. Calender roll temperatures between 150° F. and 300° F. are preferred, with a temperature of approximately 210° F. most preferred.

The superimposed webs are preferably in contact with the heated calandar rolls 30, 31 for a period of time sufficient to provide enough heat and pressure to deform the webs and partially melt the adhesives to form the laminate, but not so long as to allow any of the external adhesive coating 26 to stick to the heated roller 30. In general such times correspond to a web processing speed from about 20 to 50 feet/minute.

As described above, the ethylene oxide polymer adhesive is preferably added as a powder between the webs and on at least one surface thereof and then the precursor is conducted through the heated calender rolls as a single unit.

If desired, a cast, self-supporting film of ethylene oxide polymer can be substituted for the powder as the internal adhesive. Such a cast film can be prepared as described in U.S. Pat. No. 4,503,116 and is commercially available under the tradename QSP film distributed by Watson Foods in a film thickness of 3.5 mil. Referring to FIG. 2, in such a method, spreader 25' containing ethylene oxide polymer is replaced with a roll containing a self-supporting film of ethylene oxide polymer positioned between the feed rolls 20 and 22. The self-supporting film is then applied to lower web 12' and upper web 12 is laid thereover. The unit is then fed under spreader 25, which applies the external adhesive powder 26 and then fed through heated calender rolls 30, 31 to partially melt and deform the cast film and adhesive powder layer to form an integral matrix of thermoplastic polymer which binds the webs on interior and exterior surfaces.

In general, if the cast film is to be used as the internal adhesive material, the thickness of the cast film should be sufficient for manufacturing purposes and to adequately bond the superimposed fiber-faced webs. For this and other purposes the film thickness is preferably from about 0.5 to 5 mil.

Figure 3:
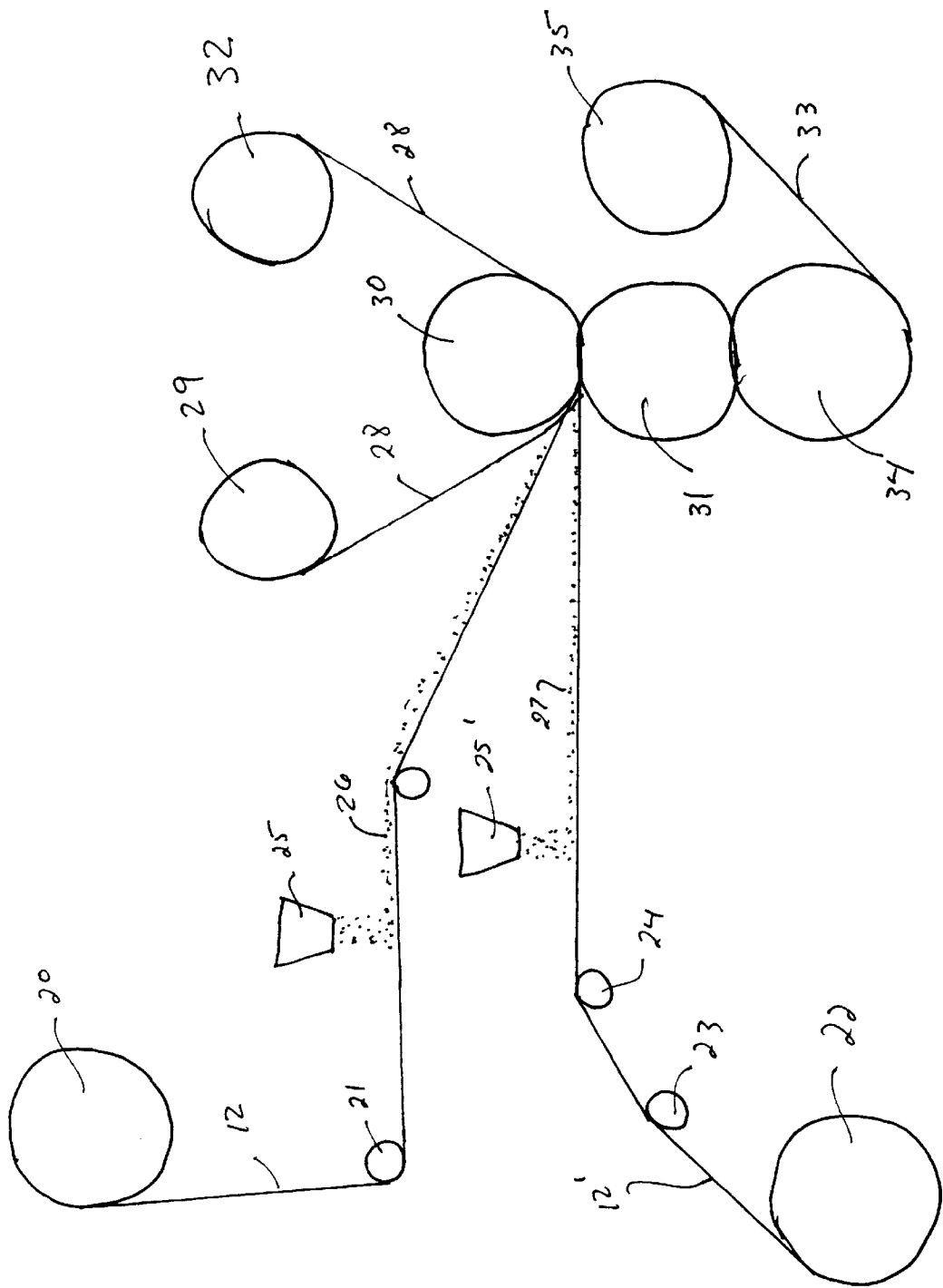
FIG. 3 is a schematic side view of the production equipment for conducting an alternative embodiment of the improved method of the invention to produce the improved dental adhesive product.

Referring to FIG. 3, a release paper 28 can be used to cover powder layer 26 and then be collected on roll 32 after passing through the nip of heated rollers 30, 31. The release paper can serve to prevent the adhesive powder layer 26 from sticking to calender roll 30 during application of heat and pressure.

Figure 4:
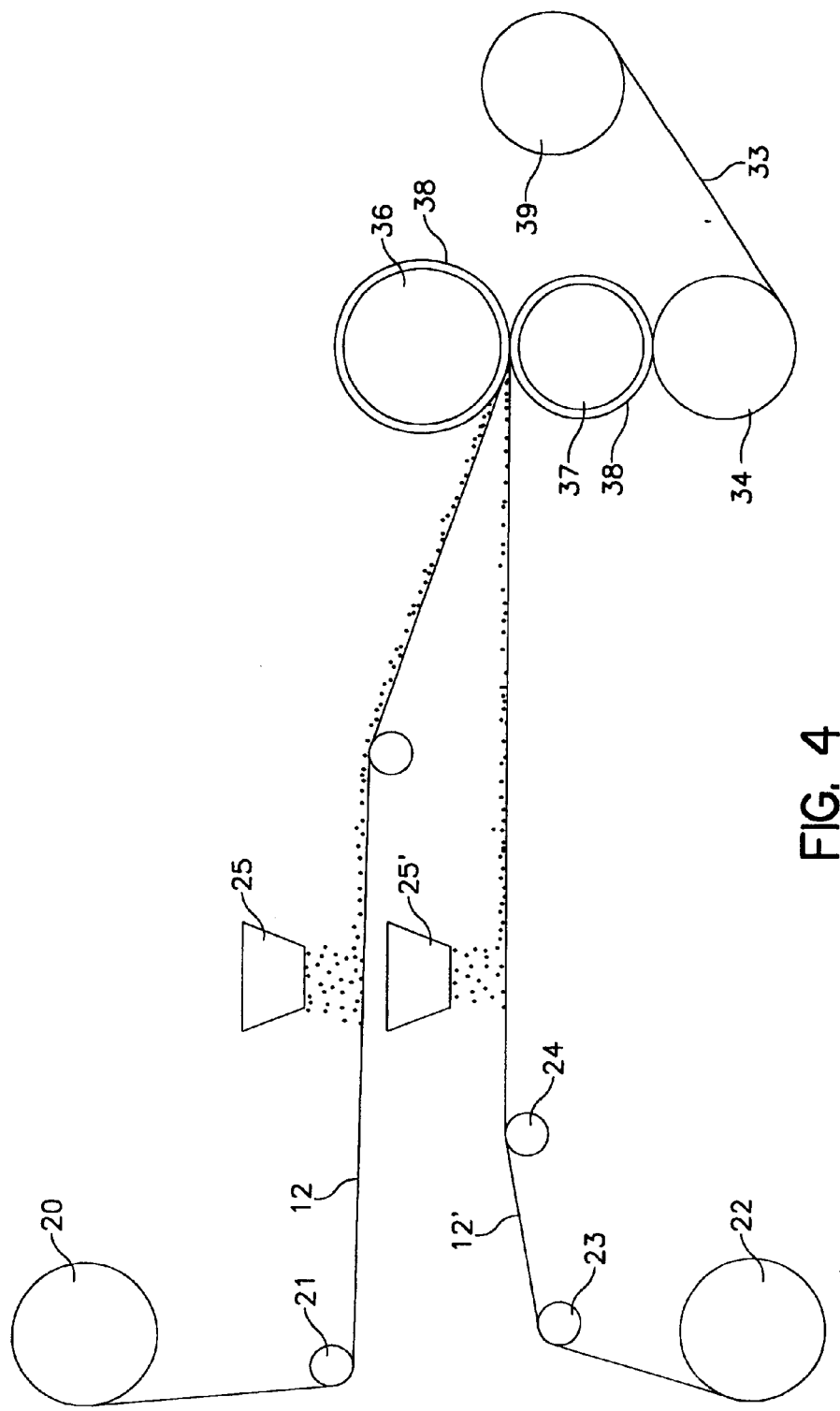
FIG. 4 is a schematic side view of the production equipment for conducting another alternative embodiment of the improved method of the invention to produce the improved dental adhesive product.

Referring to FIG. 4, TEFLON® brand polytetrafluoroethylene or similar coating can be applied to calender rolls 36, 37 to act as a release to prevent bonding of the external polymer adhesive to the heated calender rolls. In this embodiment, it is unnecessary to employ release paper or the like between the external layer and a calender roll. As seen in FIG. 4, internal and external adhesive material is applied to webs 12, 12' as in FIG. 2 from powder spreaders to form superimposed webs containing powder adhesive therebetween and thereon. Thereafter, the unit is passed through a nip between heated calender rolls 36 and 37, each which is provided with a layer of polytetrafluoroethylene or other solid lubricant as release coating 38. The resulting fused product is taken off via idler roll 34 and wound into a continuous rolled product 39.

Figure 5:
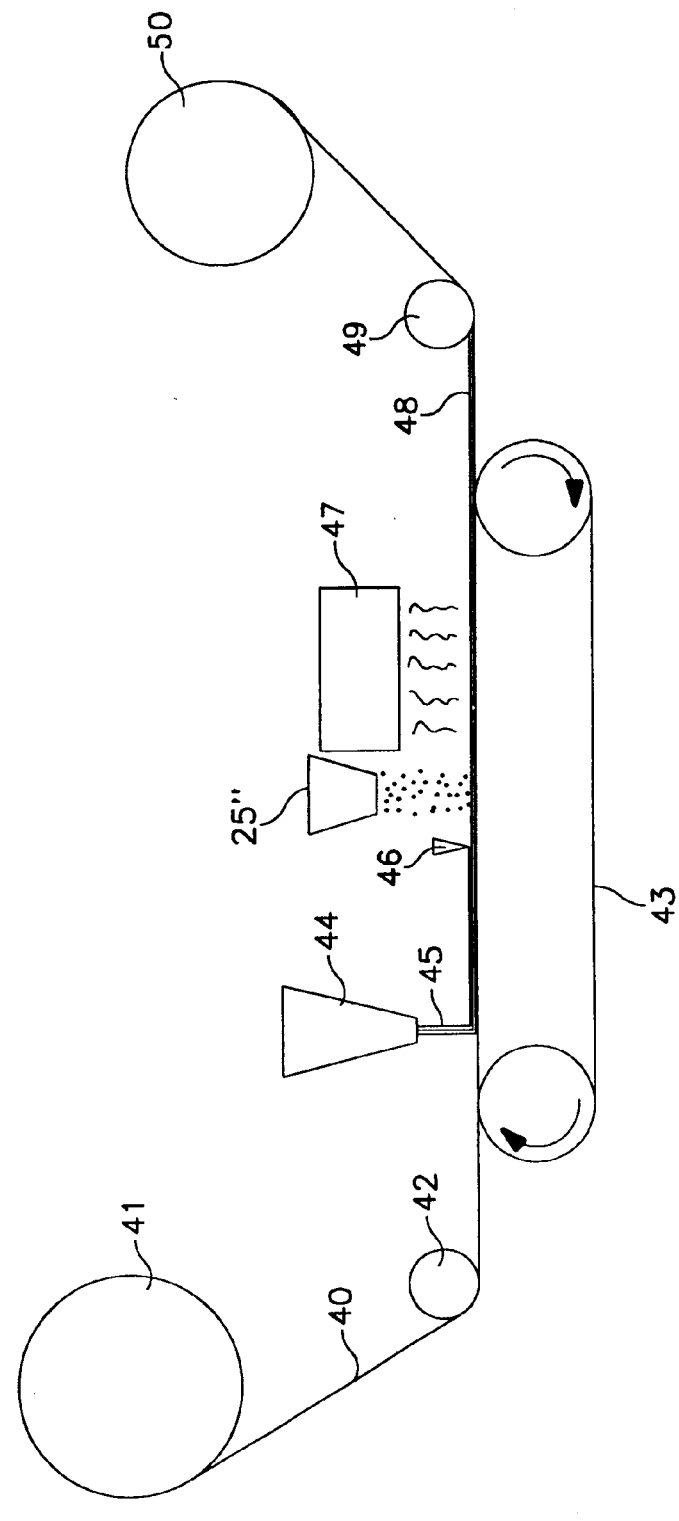
FIG. 5 is a schematic side view of the production equipment for conducting another alternative embodiment of the improved method of the invention to produce the improved dental adhesive product.
Figure 6:
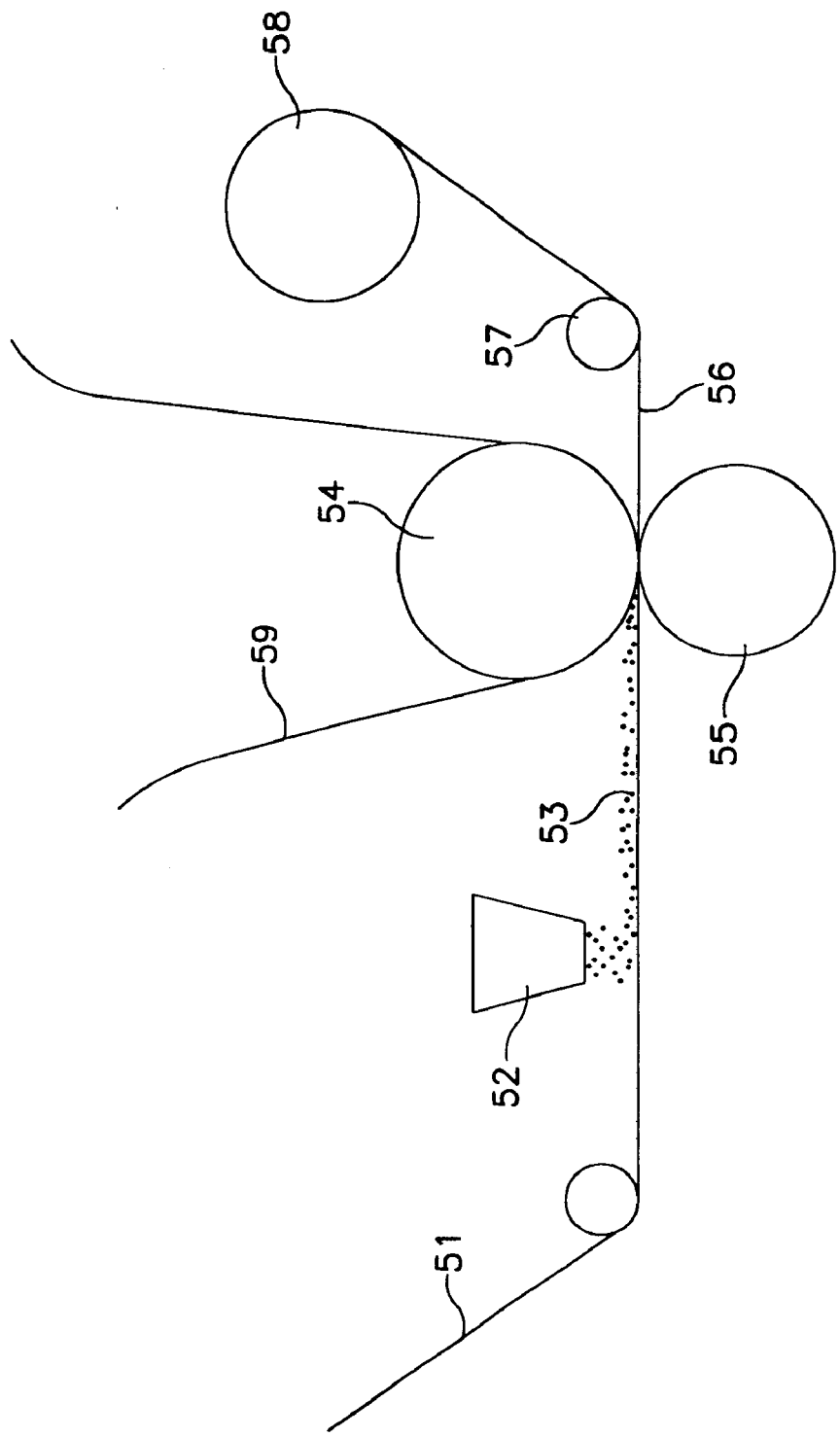
Figure 7:
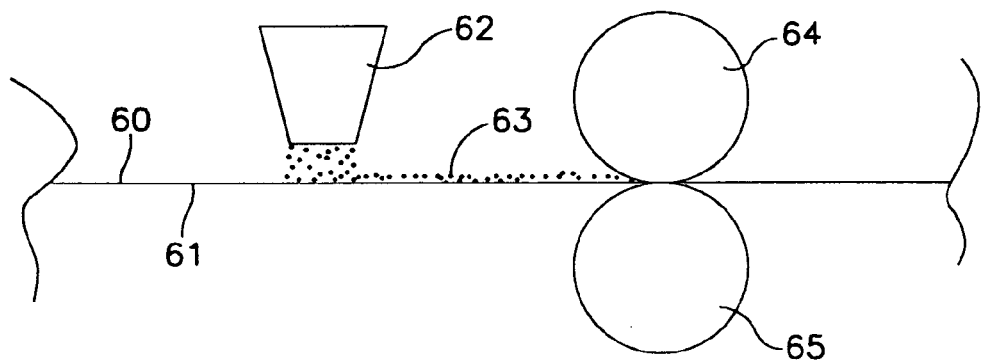
Figure 1:
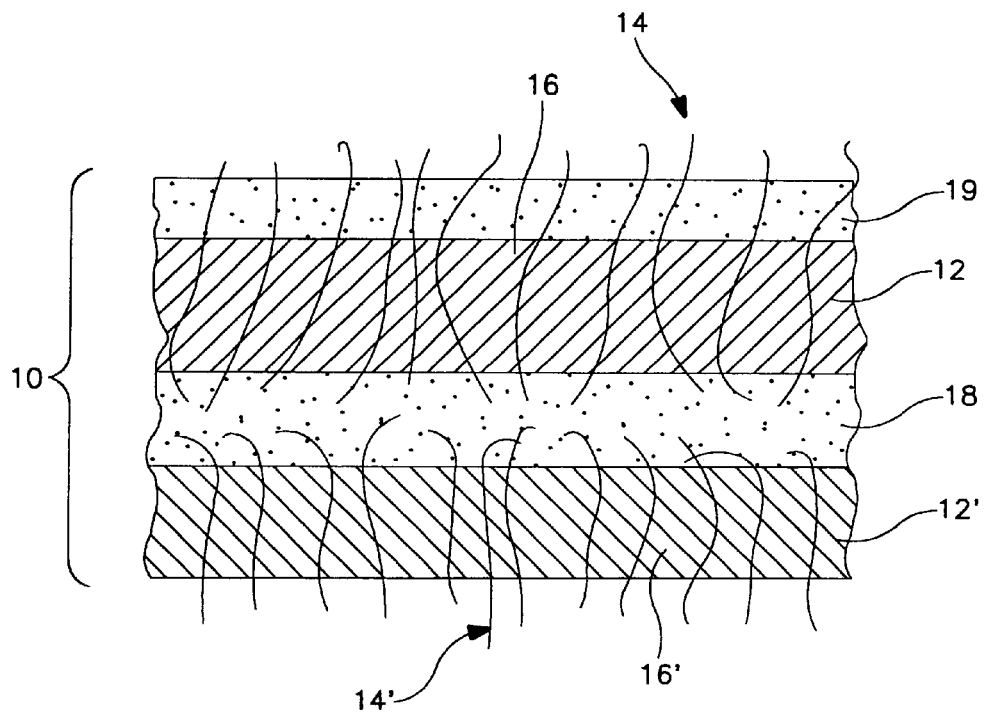
Figure 2:
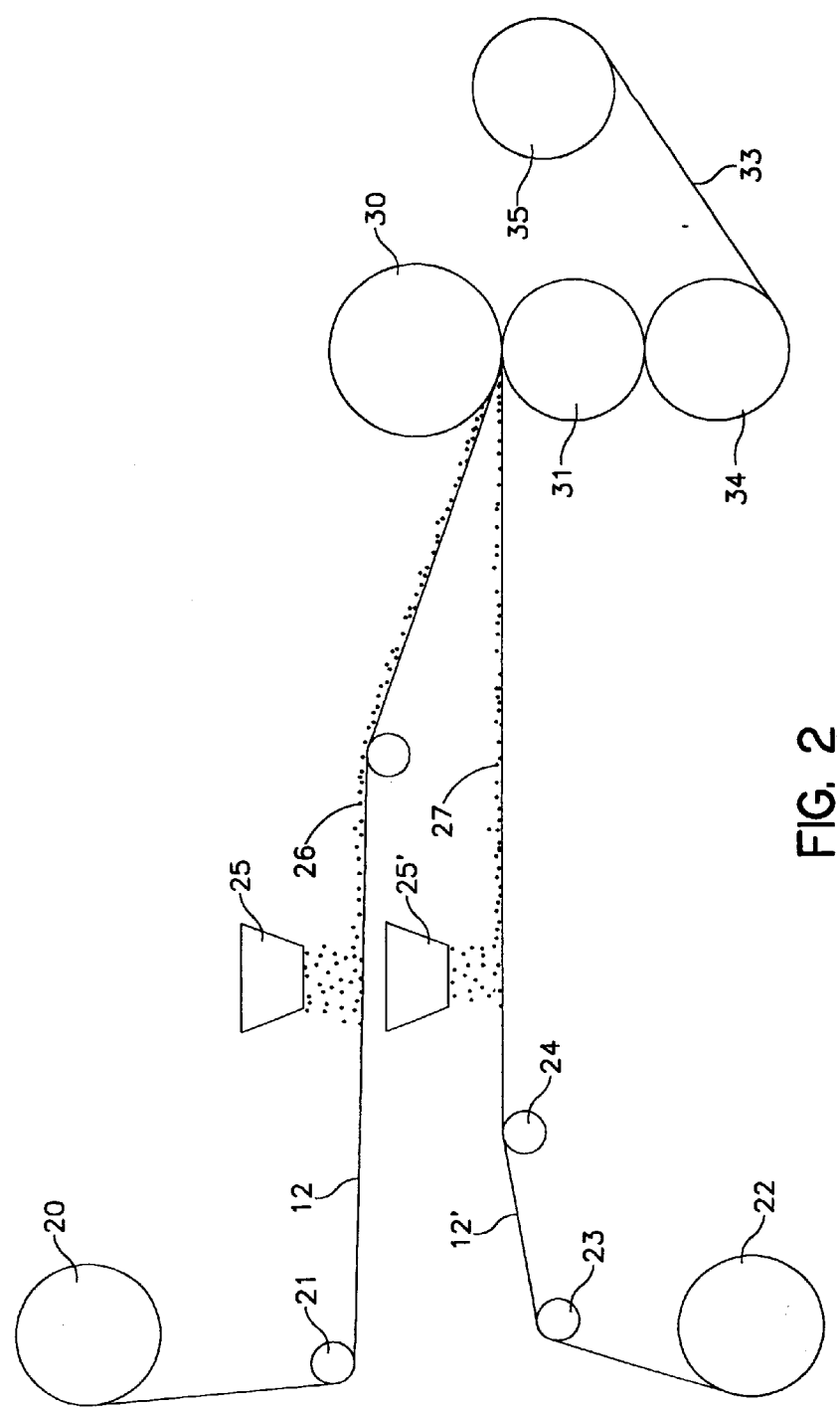
Figure 3:
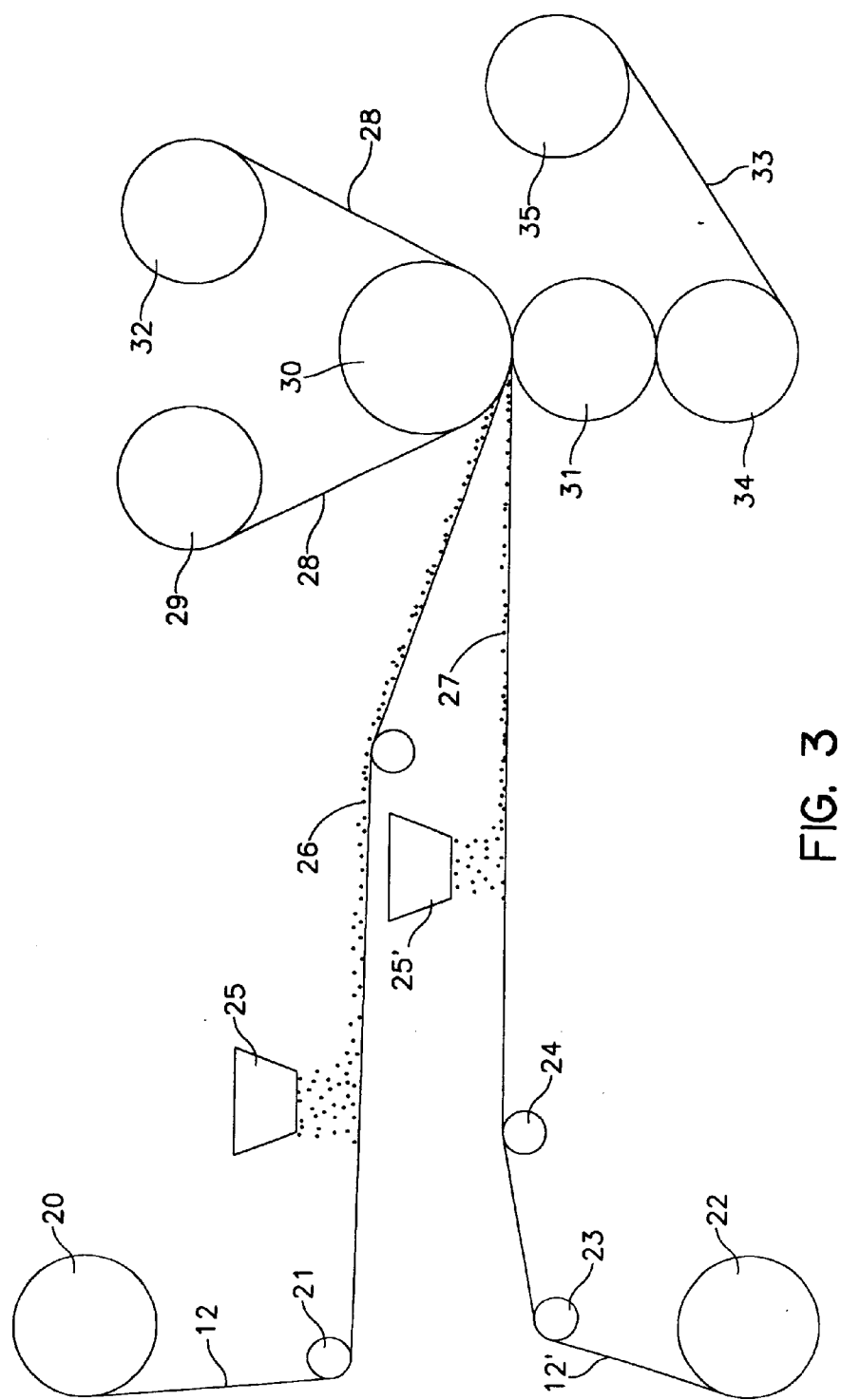
Figure 4:
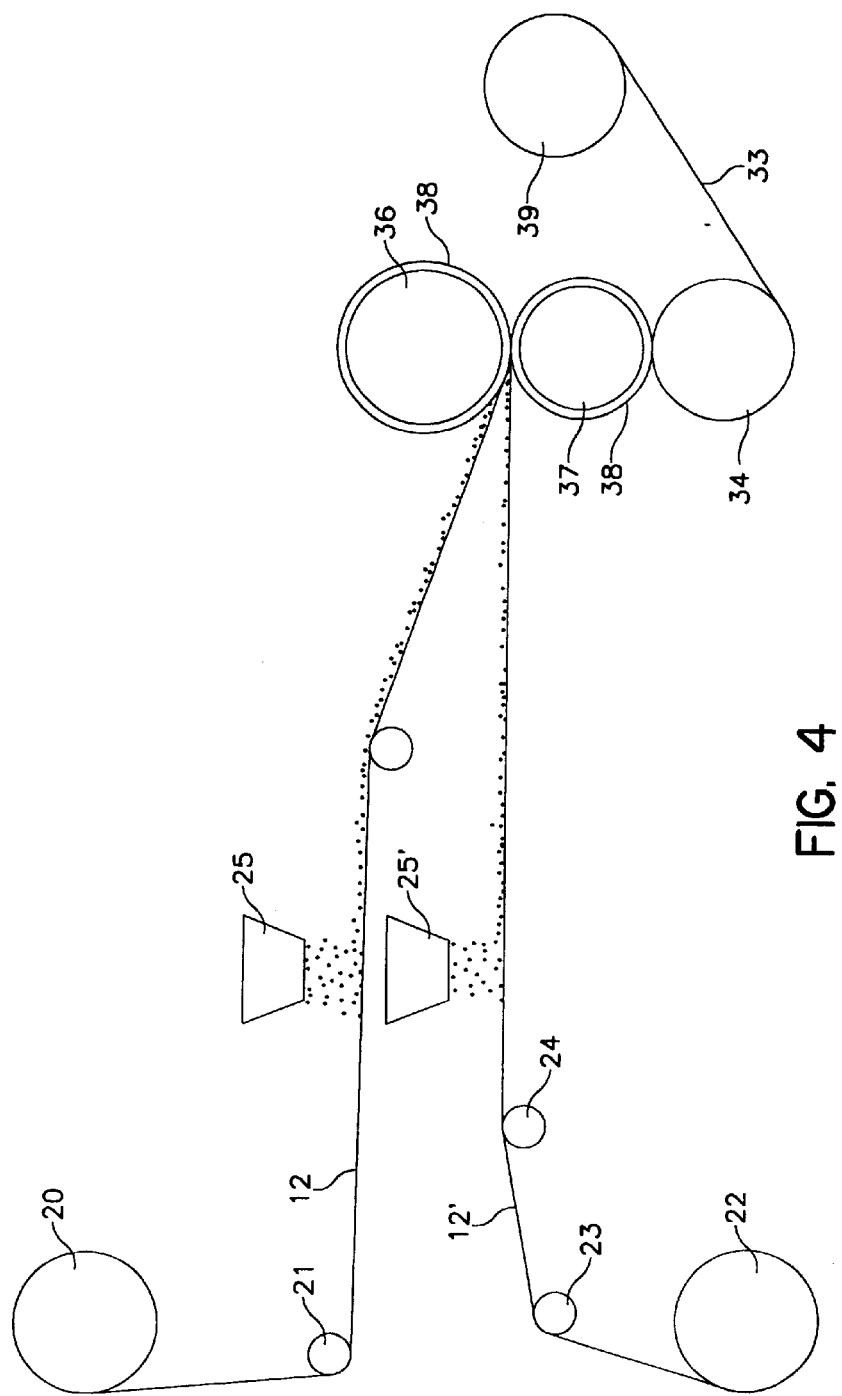
Figure 5:
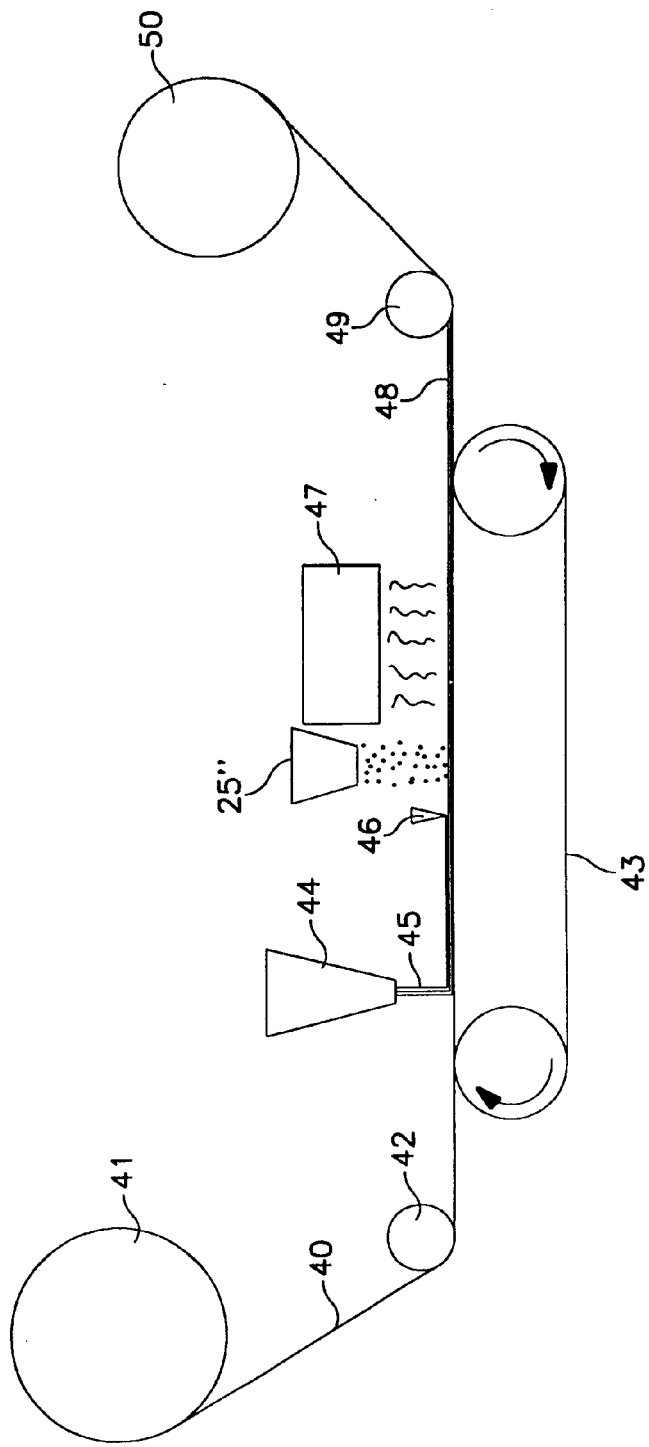
Figure 6:
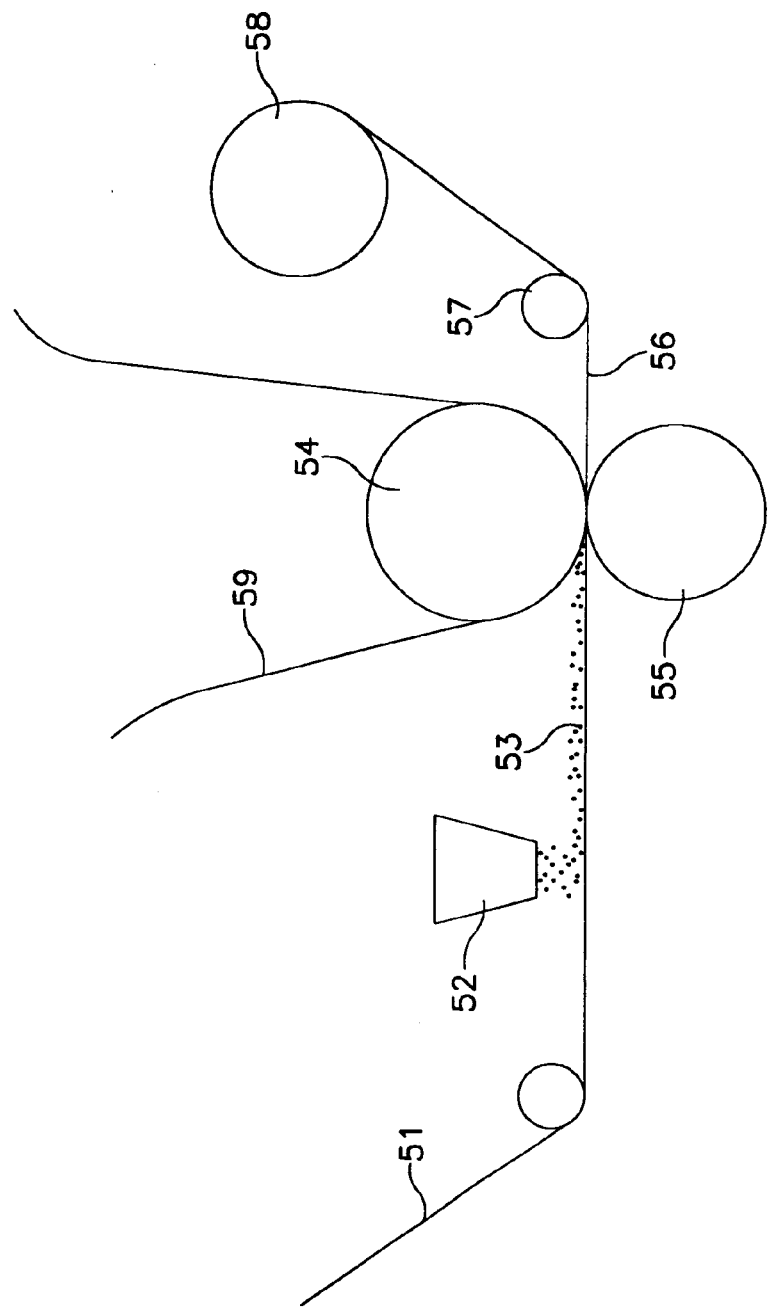
Figure 7:
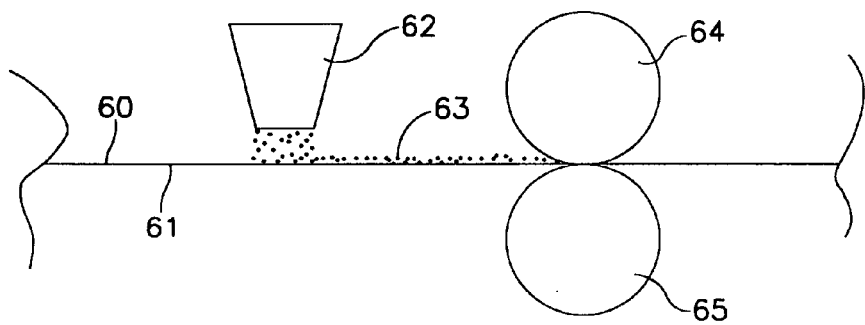

Referring to FIG. 5, in an alternative embodiment, the improved dental adhesive can be formed by applying the external adhesive matrix as a film-forming composition directly on a preformed laminate dental adhesive. A continuous strip of laminated dental adhesive product 40, such as disclosed in U.S. Pat. No. 4,503,116, has been put up as a roll of material for use in the process. The laminate 40 is fed from a roll 41 under an idler roll 42 and onto a continuous stainless steel belt loop 43. The stainless steel belt 43 conducts the preformed product 40 under liquid dispenser 44 containing a solubilized polyethylene oxide polymer adhesive 45 which applies the adhesive 45 to the upper surface of the preform 40. Although the liquid adhesive may partially penetrate the upper surface of the preform 40 to interface with the internal adhesive matrix, it remains substantially on the surface of the preform. The preform 40 containing a layer of solubilized adhesive 45 is then conducted under a doctor blade 46 which provides an adhesive layer of approximately 2 to 3 mil. The preform can then be conducted under an optional spreader 25" containing additional powder adhesive components discussed above to be added to the solublized adhesive 45. Thereafter, the preform is conducted through one or more ovens 47 to evaporate the liquid solvent from solubilized adhesive 45, thus producing a product with a dried external adhesive coating 48, which is withdrawn via a guide roll 49 and coiled up as continuous product 50.

Figure 6:
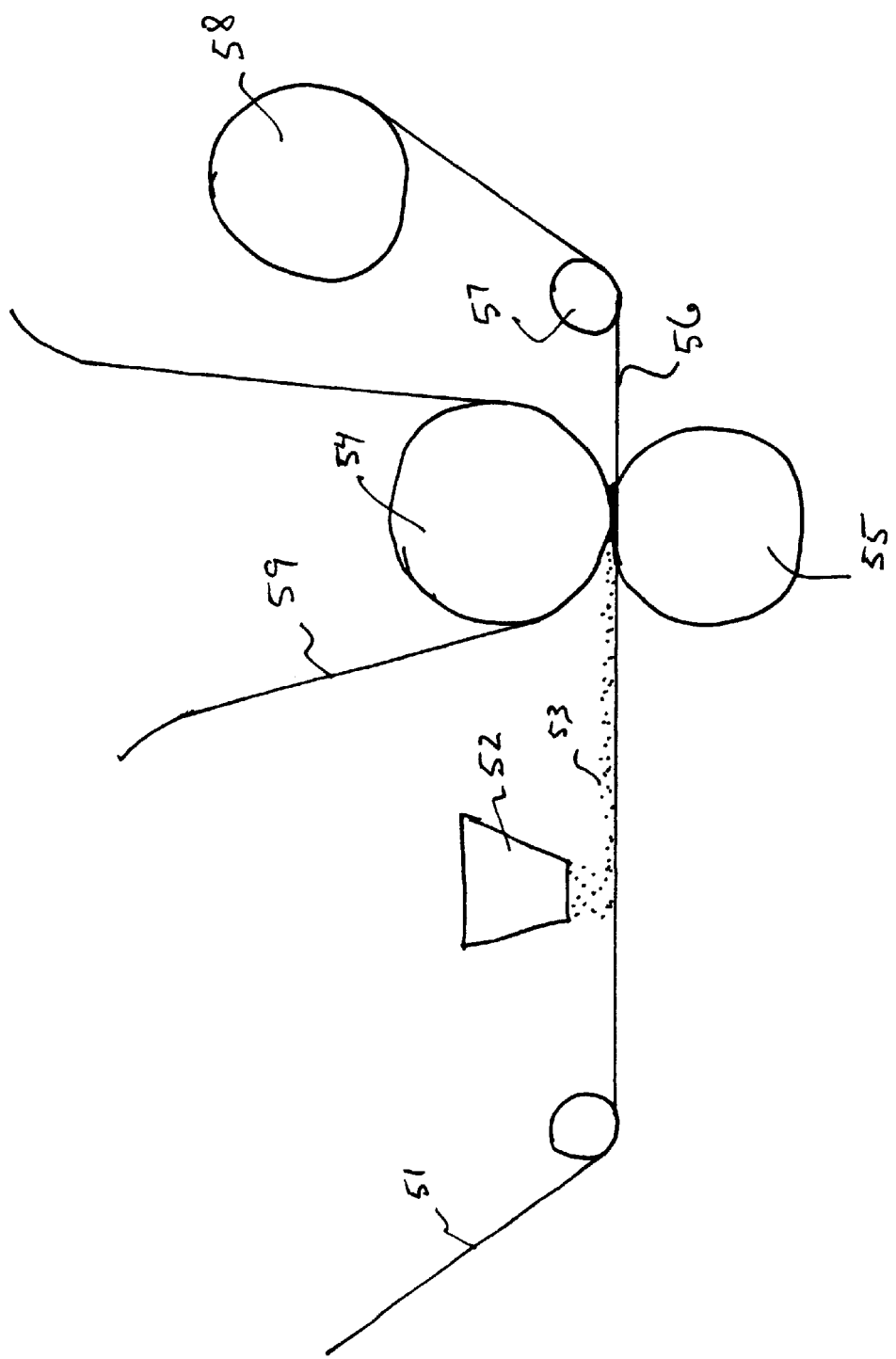
FIG. 6 is a schematic side view of the production equipment for conducting a further alternative embodiment of the improved method of the invention to produce the improved dental adhesive product.

Referring to FIG. 6, in an alternative embodiment, the improved dental adhesive can be formed by applying the external adhesive as a powder on a preformed laminate dental adhesive. Similar to FIG. 5, a continuous strip of adhesive product 51 has been put up as a roll of material for use in the process. However, instead of feeding laminate 51 under liquid dispenser and further under one or more ovens, laminate 51 is fed under powder spreader 52 which deposits ethylene oxide polymer powder layer 53 on to the upper surface of laminate 51. Laminate 51 containing the powder layer 53 is fed together with a release film 59 thereover between the nip of heated calender rolls 54, 55 wherein the powder layer 53 partially melts and thermoplastically bonds with laminate 51 forming a unitary laminate product 56 which is withdrawn via a guide roll 57 and coiled up as continuous product 58. The release film 59 is then collected (not shown). If desired, TEFLON®-coated calender rolls can be employed as in FIG. 4 to provide additional protection from the powder layer adhering to the calender rolls.

Figure 7:
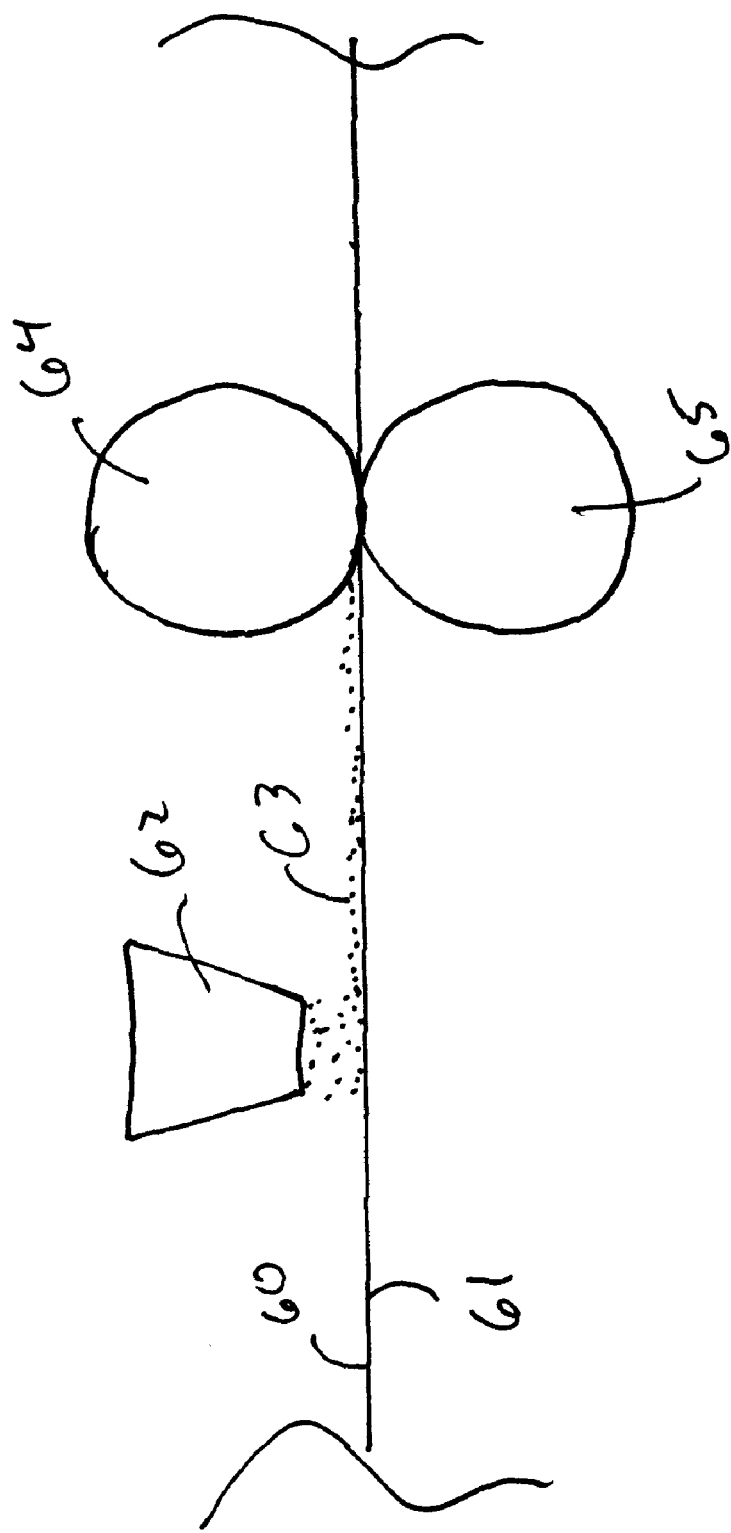
FIG. 7 is a schematic side view of the production equipment for conducting an additional alternative embodiment of the improved method of the invention to produce the improved dental adhesive product.
Figure 1:
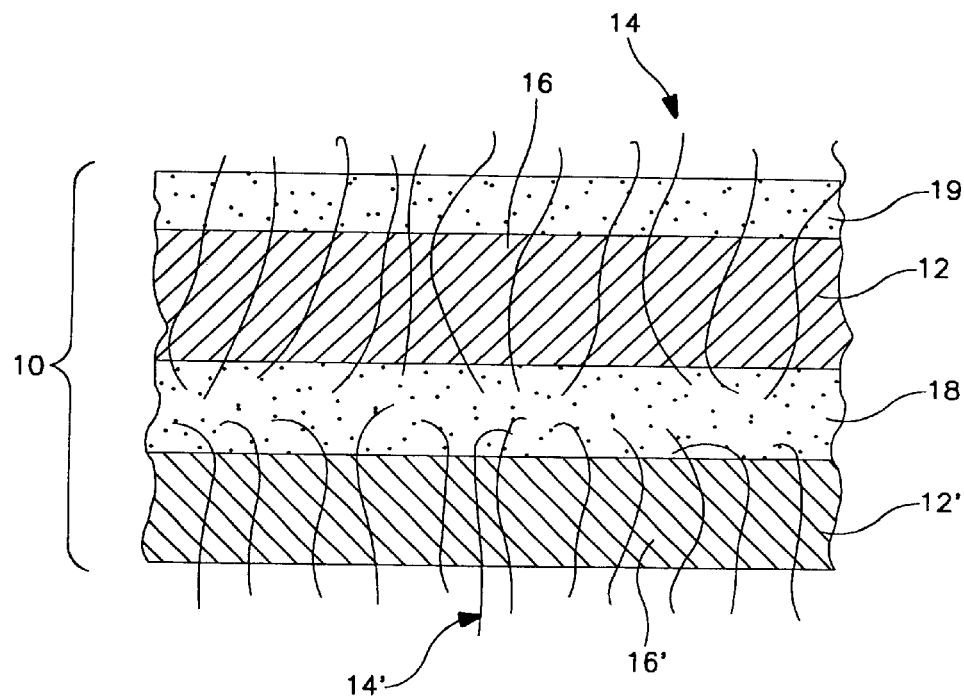
Figure 2:
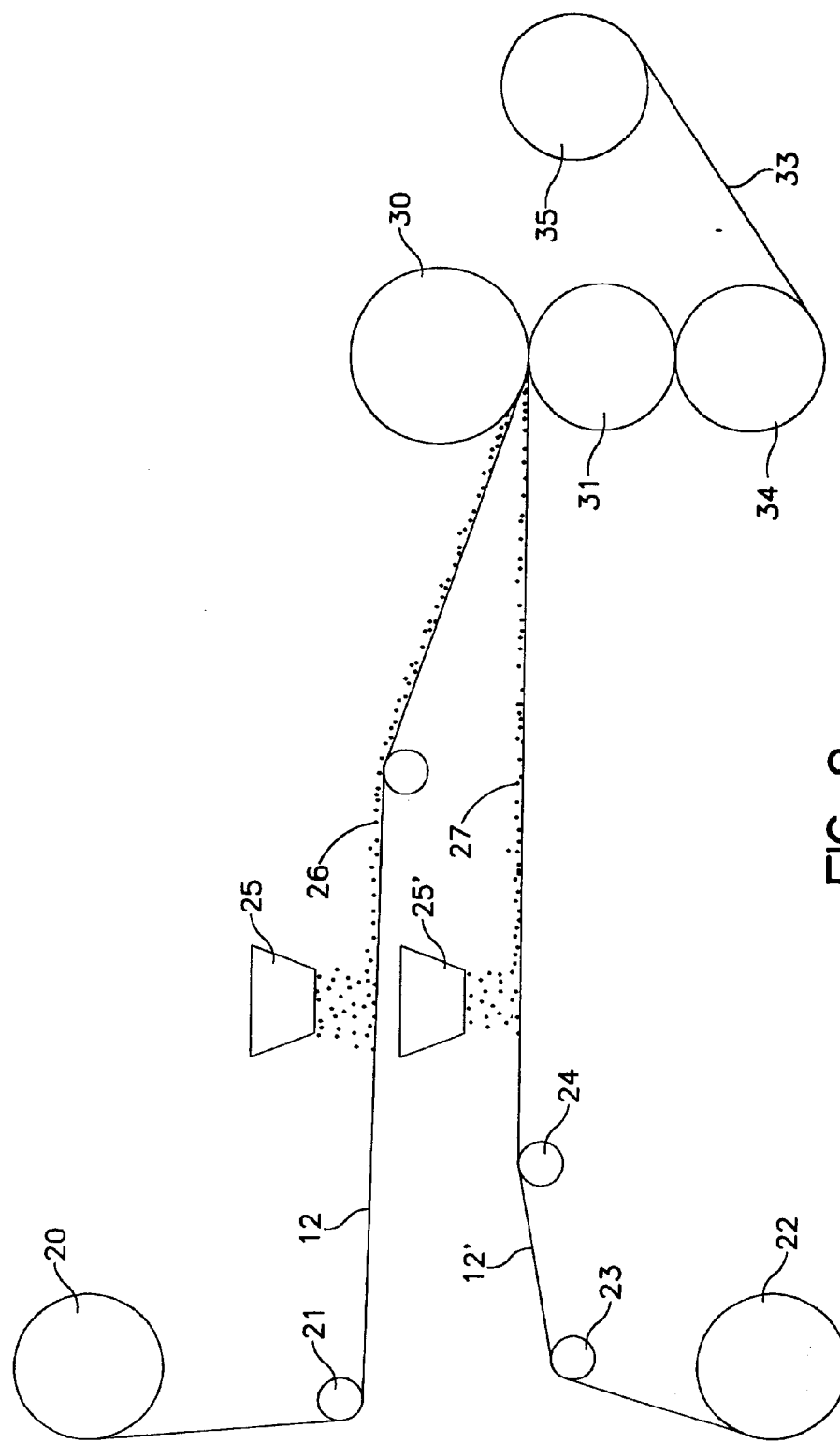
Figure 3:
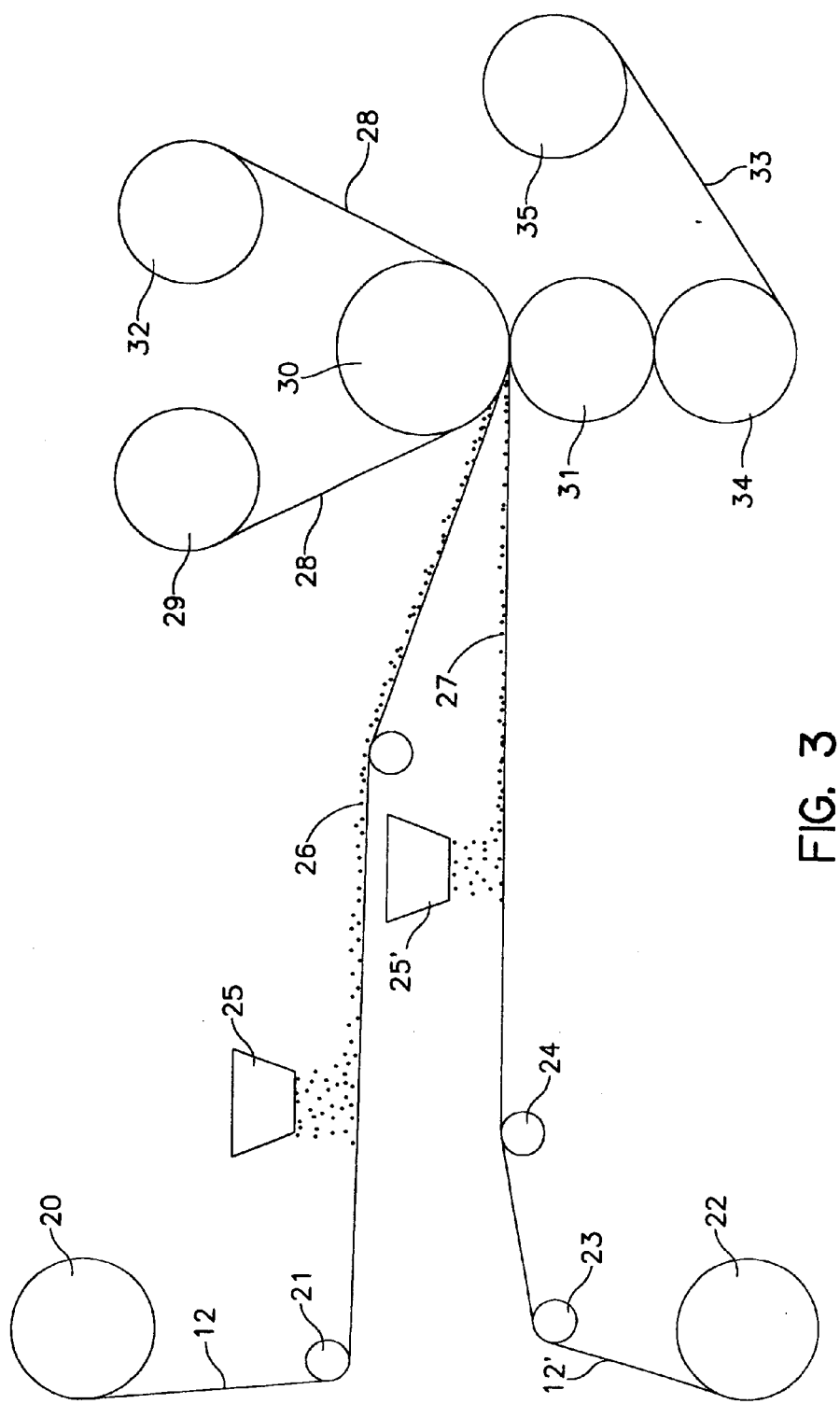

The processes described above can be modified to provide an improved dental adhesive laminate containing an external coating on both sides of the webs 12, 12'. As shown in FIG. 7, a continuous product 60 formed by the process of FIG. 4 and containing a single external adhesive layer 61 is inverted such that a free surface side of the lower web 12' faces powder spreader 62 which dispenses an ethylene oxide powder layer 63 thereon. Thereafter the precursor is passed between the nips of heated calender rolls 64, 65 to fuse layer 63 to the laminate. A release paper is typically employed as in FIG. 3 or TEFLON®-coated calender rolls can be employed as in FIG. 4 to prevent the powder layers from adhering to the calender rolls. The resulting product contains a pair of fused external adhesive layers 61, 63.

Further modifications in the production process are also possible. For example, a precursor can be made by continuously applying polyethylene oxide powder to a web and thereafter fusing the polyethylene oxide to the web. Thereafter, polyethylene oxide powder or liquid film can be applied to a second web to form a continuous layer thereon. The second web can then be applied to the fused polyethylene oxide of the first web and the webs passed through the nip of heated calender rolls to laminate the second web to the first web.

Use of a pre-cast polyethylene oxide-containing film as the external layer is possible, but results have been less satisfactory than with powder or liquid film which are preferred.

A typical weight of the resulting product of the processes discussed above with a single external coat is about 6.6 ounces per square yard. Of this, the webs comprise about 3.6 ounces (two pieces of 1.8 ounces each), and the ethylene oxide polymer or the water-activated adhesive/ethylene oxide polymer blend is about 3.0 ounces. The additional coating will contribute an additional approximately 0.3 to approximately 3.0 ounces per square yard, depending on the amount of additional adhesive coating applied. Thus, the product containing an external coating on both sides can weigh from approximately 6.9 to approximately 9.6 ounces per square yard and preferably weighs approximately 7.4 ounces per square yard. The thickness of the single sided product ranges from about 0.014 inch to about 0.02 inch and, for the double sided product, from about 0.021 inch to about 0.028 inch.

The resulting products are improved dental adhesive laminates with excellent characteristics, including increased "holding power" due to the external adhesive coating. The products are designed to bond the denture to the gum longer than conventional laminated dental adhesive prior art products. Further, the instant products retain their water-activated adhesives better to permit the dental adhesive products to more effectively bond a denture to the gums.

The improved dental adhesive product is typically 45 inches wide when produced. Thereafter it is slit to a width of 22½ inches for convenient handling. Typically, the product is rolled up on cores for shipment. No drying or other processing is conducted, nor are other chemicals added. The rolled goods are thereafter die-cut into the appropriate shapes for use as dental adhesives and packed for sale.

When inserted in the oral cavity to secure dentures, the improved dental adhesives of this invention containing an external adhesive coating on only one side are preferably applied with the side containing the external adhesive contacting the denture. However, improved holding results can also be achieved when the external coating of the dental adhesive contacts the oral cavity.

The following Examples are not intended, and should not be interpreted, to limit the scope of this invention but are provided to further illustrate certain preferred embodiments of the invention.

EXAMPLE 1

Five trials were conducted to test the present improved product which was made by a method similar to that described in FIG. 6. The improved dental adhesive product was formed by applying ethylene oxide polymer powder to an existing prior art laminate dental adhesive known in the art as SEA-BOND® denture adhesive sold by Combe, Inc. Four different adhesive powder blends were used as the external coating, wt %/wt %, (i) 5% polyethylene oxide ("polyox") and 95% carboxymethyl cellulose ("CMC"), (ii) 10% polyethylene oxide and 90% carboxymethyl cellulose, (iii) 20% polyethylene oxide and 80% carboxymethyl cellulose, and (iv) 50% polyethylene oxide and 50% carboxymethyl cellulose. Two DuPont TEFLON® films (200 ft FEP 100 A×24" DuPont Mill Roll #9419314) were used as release films over the powder layer, one at 1 mil thickness and the other at 0.5 mil thickness (Supplier: American Durafilm Co., Inc.).

The first trial used a single sheet of SEA-BOND® brand scrim denture adhesive laminate formed by laminating a pair of webs sandwiching an adhesive composition having the following composition:

TABLE 1

| Adhesive Components | Oz. Per Sq. Yard | Percent | ** % Active |
|---|---|---|---|
| Kelvis (Sodium Alginate) Kelco | 0.750 | 11.361 | a |
| Polyox WSR-301 (100 mesh) | 0.750 | 11.361 | a |
| Sodium copper Chlorophyll | 0.001 | 0.015 | a |
| Web Components | | | |
| Non-woven roll goods (National Felt**) | | | i |
| Cellulose Acetate Fiber | 2.400 | 36.358 | |
| Hemp | 1.140 | 17.270 | |
| Poly Vinyl Alcohol | 0.060 | 0.908 | |

The TEFLON® release film 59 was only 24" wide compared to the 40" wide scrim; therefore a portion of the powder hopper 52 was blocked off using a piece of felt to prevent powder from depositing directly on the scrim beyond the release media. The loading of the adhesive powder applied to the top surface of the scrim was 4 ounces of powder blend by 24 inch wide scrim. This combination was run for about 15 minutes with no powder or TEFLON® sticking to the rolls.

The second trial used the 0.5 mil TEFLON® release film and the 10% polyox/90% CMC blend and the same operating conditions as the first trial. This trial was run for about 10 minutes with no powder or TEFLON® sticking to the rolls.

The third trial used the 0.5 mil TEFLON® release film and the 10% polyox/90% CMC blend. This trial used a 7" wide SEA-BOND® scrim powder sandwich. This trial was run for about 5 minutes with no powder or TEFLON® sticking to the rolls.

The fourth trial used 0.5 mil TEFLON® release film and the 20% polyox/80% CMC blend. A roll of SEA-BOND® scrim denture adhesive laminate was used for this trial, but without cutting the fabric as normally would have been done. This trial was run for about 5 minutes with no sticking to the rolls.

The fifth trial used 1 mil TEFLON® release film and a 50% polyox/50% CMC blend. This combination was run for about 5 minutes without anything sticking to the rolls.

EXAMPLE 2

Samples of the improved denture adhesive product of this invention containing an external coating of adhesive were tested in an in vitro experiment for adhesion strength in comparison to prior art dental adhesive laminates that did not contain the external adhesive coating. Samples were prepared as in Example 1, by applying either a 50:50 (wt./wt.) mixture or a 20:80 (wt./wt.) mixture of polyethylene oxide and carboxymethyl cellulose as a powder layer to one side of a preformed, prior art SEA-BOND® brand dental adhesive laminate which was then combined with a TEFLON® release paper (0.5 mil) and the precursor fed between the nip of heated calendar rolls to produce an improved dental adhesive product having a single side of external adhesive. Table 2 provides a typical formulation for the improved dental adhesive with a 50:50 mixture of external adhesive.

TABLE 2

| Internal Adhesive | Oz. Per Sq. Yard | Percent | ** % Active |
|---|---|---|---|
| Kelvis (Sodium Alginate) Kelco | 0.750 | 11.361 | a |
| Polyox WSR-301 (100 Mesh) | 0.750 | 11.361 | a |
| Sodium copper Chlorophyll | 0.001 | 0.015 | a |
| Web components | | | |
| Non-woven roll goods (National Felt**) | | | i |
| Cellulose Acetate Fiber | 2.400 | 36.358 | |
| Hemp | 1.140 | 17.270 | |
| Poly Vinyl Alcohol | 0.060 | 0.908 | |
| ** (Uses Dexter non-viscose #13208) | | | |
| External Coating | | | |
| Polyox WSR-301 (100 mesh) | 0.750 | 11.361 | a |
| Carboxymethyl cellulose 7H3SXF (Aqualon) | 0.750 | 11.361 | |
| | 6.601 | 100.000 | |

The webs and internal adhesive are present in the preformed SEA-BOND® dental adhesive laminate. The polyox and CMC in a 50:50 mixture were deposited as a blend on the upper layer of the SEA-BOND® dental adhesive laminate. Samples having a 20:80 mixture polyethylene oxide and carboxymethyl cellulose external adhesive layer were prepared in the same way.

An Instron Model 1011 was used to measure the tensile adhesion of the improved denture adhesive products. This instrument measures the actual tensile adhesion in pounds of force of the denture adhesive. The Instron was connected to a computer that controls the parameters for the adhesive testing, which were entered in the computer as follows:

1) The Instron was calibrated to measure 0–100 pounds of load at peak (tensile strength).
2) The pulling speed of the Instron was 5 inches per minute (cross-head speed).
3) The sample rate (points/second) was 20.
4) This square area of the sample was 6.12 square inches, measured by a Nikon Digipad.
5) Grip distance was 7.5 inches (pin to pin) top fixture to bottom fixture.

The sample fixture was a combination of an upper and lower part in between which the denture adhesive samples are sandwiched. On the upper part, a chamois material was draped over and pulled skin tight by the use of a spring to create a collagen surface. The upper part was affixed to the Instron with a pin.

The lower part of the sample fixture was the base which during testing was permanently fixed to the Instron with a pin. At the face of the fixture was a 3.5" diameter acrylic pad that matches the 3.5" chamois surface of the upper part of the fixture.

The chamois surface was rinsed with de-ionized distilled water and then dried with a paper towel leaving the surface damp. The denture adhesive wafer sample is then soaked at ambient room temperature in saline solution (9 gms, NaCl to 1,000 mls. de-ionized, distilled water) for one (1) minute. The wafer was removed with forceps and placed evenly on the chamois surface for wetting out purposes for one (1) minute. The upper fixture with the wetted-out wafer was then placed on the acrylic surface and aligned by lowering the upper grip of the Instron to match exactly with the pin hole of the upper fixture with the Instron grip hole. The upper grip was then raised up leaving the upper and lower fixture pressed together. At this stage a five (5) pound weight was placed on the top of the upper fixture for three (3) minutes. At the end of three (3) minutes the weight was removed and the upper grip was lowered to replace and secure the pin.

When the pin was secured, the Instron was engaged through the computer and the sample is pulled apart. All the relevant data was measured by the computer and printed out. At the end of each test sample the fixture surfaces were washed and then rinsed thoroughly with de-ionized distilled water, dried with a paper towel and readied for the next sample.

The average tensile strength values and the standard deviations for each of the samples obtained from the statistical analyses are summarized in Table 3.

TABLE 3

| Formula | Adhesion Strength (lbs.) | No. of Samples Tested |
|---|---|---|
| Reference Sample | 15.46 ± 2.8 | 11 |
| 50% Polyox[1] 50% CMC[2] | 32.77 ± 6.2 | 18 |
| 20% Polyox 80% CMC | 27.63 ± 4.0 | 12 |

[1]"Polyox" is polyethylene oxide polymer
[2]"CMC" is carboxymethyl cellulose

As demonstrated in Table 3, the improved product of the invention provides significantly improved bonding over the conventional laminates formed without an external adhesive layer. The results show an 80% to 100% improvement in adhesive strength by the improved product over the conventional laminate.

EXAMPLE 3

An in vivo test was conducted to compare the holding ability of the improved dental adhesive product containing an external adhesive coating comprising a 50:50 (wt./wt.) mixture of polyethylene oxide and carboxymethyl cellulose with that of a conventional laminated dental adhesive as recited in Table 1. A total of 209 human volunteers who had previously used dental adhesive laminates without an external adhesive were asked to compare the instant improved product to the conventional dental adhesive laminate by using both products individually to secure dentures in their mouths. Of these, 105 volunteers were given the improved dental adhesive composition containing external adhesive on one side and 104 volunteers were given the improved dental adhesive composition with external adhesive on two sides. The dental adhesive compositions comprising a single side of external adhesive were prepared by a method similar to the method described in FIG. 2 and those containing double sided external adhesive by a method similar to the method described in FIG. 6. Volunteers using the one-sided product were instructed to position the product so that the external adhesive contacted the denture.

Based on interviews of the volunteers, the in vivo test demonstrated that the improved product containing either a single or double side of external adhesive provided a much better bond than the prior art dental adhesive laminate and the bond lasted much longer than the prior art laminate by a margin of at least 2 to 1. It was noted that both the single and double sided external adhesive variants bonded the denture to the gums so strongly that they were seen as being harder to remove after use.

Although certain preferred embodiments have been described, it will be evident that changes may be made in the steps of the processes and components and details of the product without departing from the spirit and principles of the inventions.

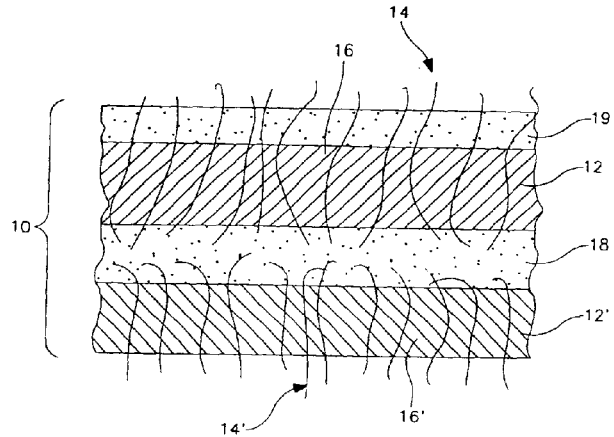

What is claimed is:

1. A dental adhesive product comprising a laminate of a pair of superimposed fiber-faced webs, each web having an external and an internal surface with fibers held therein and protruding therefrom to present a fiber facing on each surface of each of said webs, a first ethylene oxide polymer composition sandwiched between said internal surfaces of said webs, and a second ethylene oxide polymer composition dispersed on said external surface of at least one of said webs.

2. The dental adhesive product of claim 1 in which at least one of the first or second ethylene oxide polymer compositions is a film composition.

3. The dental adhesive product of claim 1 in which a dry water-activated adhesive is additionally present between said webs.

4. The dental adhesive product of claim 1 in which a dry water-activated adhesive is additionally present on the external surface of at least one of said webs.

5. The dental adhesive product of claim 1 in which a dry water-activated adhesive is additionally present on the external surface of both said webs.

6. The dental adhesive product of any of claims 3–5 in which the dry water-activated adhesive is a powder layer.

7. The dental adhesive product of any of claims 3–5 in which the dry water-activated adhesive is sodium alginate.

8. A method for producing a dental adhesive product comprising:
   a) applying a first thermoplastic ethylene oxide polymer composition to a surface of a first fibrous web;
   b) contacting the first web with a second fibrous web in superimposed relation to form a composition whereby said first ethylene oxide polymer composition is arrayed between and contacts said first and second webs;
   c) applying a second thermoplastic ethylene oxide polymer composition to at least one surface of the first or second webs opposite to the surface contacting the first ethylene oxide polymer composition; and
   d) forming a unitary laminate of said first and second ethylene oxide polymer compositions and said first and second webs.

9. The method of claim 8 in which at least one of the first or second ethylene oxide polymer compositions is applied as a film.

10. The method of claim 8 in which a dry water-activated adhesive is added to at least one of the first or second thermoplastic ethylene oxide polymer composition.

11. The method of claim 10 in which a dry water-activated adhesive is added to the first thermoplastic ethylene oxide polymer composition prior to step (b).

12. The method of claim 10 in which a dry water-activated adhesive is added to the second thermoplastic ethylene oxide polymer composition prior to step (d).

13. The method of claim 8 in which a dry water-activated adhesive is applied as a powder layer on a surface of at least one of the films.

14. The method of any of claims 10–13 in which the dry water-activated adhesive is sodium alginate.

15. A method for producing a dental adhesive product comprising:
   a) applying a first thermoplastic ethylene oxide polymer composition to a surface of a first fibrous web;
   b) contacting the first web with a second fibrous web in superimposed relation to form a composition whereby said first ethylene oxide polymer composition is arrayed between and contacts said first and second webs;
   c) forming a first unitary laminate of said first ethylene oxide polymer composition and said first and second webs;
   d) applying a second thermoplastic ethylene oxide polymer composition to at least one surface of said first unitary laminate; and
   e) forming a second unitary laminate from said second ethylene oxide polymer composition and said first unitary laminate.

16. The method of claim 15 in which at least one of the first or second ethylene oxide polymer compositions is applied as a film.

17. The method of claim 15 in which a dry water-activated adhesive is added to at least one of the first or second thermoplastic ethylene oxide polymer composition.

18. The method of claim 17 in which a dry water-activated adhesive is added to the first thermoplastic ethylene oxide polymer composition prior to step (b).

19. The method of claim 15 in which a dry water-activated adhesive is added to the second thermoplastic ethylene oxide polymer composition prior to step (e).

20. The method of claim 15 in which a non-binding release paper is superimposed over said second thermoplastic ethylene oxide polymer composition prior to step (e).

21. The method of claim 15 in which a dry water-activated adhesive is applied as a powder layer on a surface of at least one of the films.

22. The method of any of claims 17–21 in which the dry water-activated adhesive is sodium alginate.

* * * * *

UNITED STATES PATENT AND TRADEMARK OFFICE
CERTIFICATE OF CORRECTION

PATENT NO. : 6,638,881 B2
DATED : October 28, 2003
INVENTOR(S) : Herbert Lapidus It is certified that error appears in the above-identified patent and that said Letters Patent is hereby corrected as shown below:

Title page,
Delete and substitute there the attached title page as shown on the attached page.

Drawings,
Delete sheets 1-7 and substitute therefore the drawing sheets, consisting of Figs 1-7 as shown on the attached pages.

Signed and Sealed this

Twenty-fourth Day of August, 2004

JON W. DUDAS
*Director of the United States Patent and Trademark Office*

(12) United States Patent
Lapidus

(10) Patent No.: US 6,638,881 B2
(45) Date of Patent: Oct. 28, 2003

(54) DENTAL ADHESIVE DEVICE AND METHOD OF PRODUCING SAME

(75) Inventor: Herbert Lapidus, Ridgefield, CT (US)

(73) Assignee: Combe Incorporated, White Plains, NY (US)

(*) Notice: Subject to any disclaimer, the term of this patent is extended or adjusted under 35 U.S.C. 154(b) by 255 days.

(21) Appl. No.: 09/747,805

(22) Filed: Dec. 22, 2000

(65) Prior Publication Data

US 2002/0006980 A1 Jan. 17, 2002

Related U.S. Application Data

(60) Provisional application No. 60/171,592, filed on Dec. 23, 1999.

(51) Int. Cl.$^7$ ............................................. B32B 27/12
(52) U.S. Cl. ................... 442/149; 442/151; 442/393; 442/394; 428/343; 156/278; 156/283
(58) Field of Search ................... 428/343; 442/394, 442/393, 149, 151; 156/278, 283

(56) References Cited

U.S. PATENT DOCUMENTS

| | | | |
|---|---|---|---|
| 2,897,593 A | 8/1959 | Hollander et al. | 32/2 |
| 2,978,812 A | 4/1961 | Rosenthal et al. | 32/2 |
| 3,575,915 A | 4/1971 | Novak et al. | 260/29.6 |
| 3,868,340 A | 2/1975 | Keegan et al. | 260/17.4 |
| 3,990,149 A | 11/1976 | Nedwig | 32/2 |
| 4,503,116 A | 3/1985 | Lapidus | 428/286 |
| 4,608,088 A | 8/1986 | Lokken | 106/35 |
| 4,632,880 A | 12/1986 | Lapidus | 428/523 |
| RE33,093 E | 10/1989 | Schiraldi et al. | 424/676 |
| 4,880,702 A | 11/1989 | Homan et al. | 428/354 |
| 5,166,233 A | 11/1992 | Kuroya et al. | 524/37 |
| 5,209,777 A | 5/1993 | Altwirth | 106/35 |
| 5,369,145 A | 11/1994 | Gasman et al. | 523/120 |
| 5,525,652 A | 6/1996 | Clarke et al. | 524/37 |
| 5,624,745 A | 4/1997 | Lapidus | 428/308.8 |
| 5,658,586 A | 8/1997 | Rajaiah et al. | 424/435 |

FOREIGN PATENT DOCUMENTS

| | | |
|---|---|---|
| EP | 0353375 | 8/1988 |
| EP | 0396411 | 11/1990 |
| JP | 63 54318 | 3/1988 |
| JP | 149110 | 5/1992 |
| JP | 65210 | 3/1993 |
| JP | 65211 | 3/1993 |

Primary Examiner—Elizabeth M. Cole
(74) Attorney, Agent, or Firm—Fitzpatrick, Cella, Harper & Scinto

(57) ABSTRACT

An improved dental adhesive device to hold prosthetic devices in the human mouth is made as a laminate of webs which are bonded together by deforming a film of thermoplastic ethylene oxide polymer and having an external adhesive coating on the laminate. The dental adhesive is produced by continuously applying thermoplastic ethylene oxide polymer between moving webs of cellulose acetate fibers, applying additional thermoplastic ethylene oxide polymer to the external surface of the webs, and then passing said webs in superimposed relationship between a pair of dry heated calender rolls for thermoplastically bonding said webs into a unitary structure. A dry water-activated adhesive material, such as sodium alginate, may be employed with the thermoplastic ethylene oxide polymer by being dissolved or dispersed in the polymer. Synthetic fibers are applied to the webs so as to extend transversely through the webs.

22 Claims, 7 Drawing Sheets

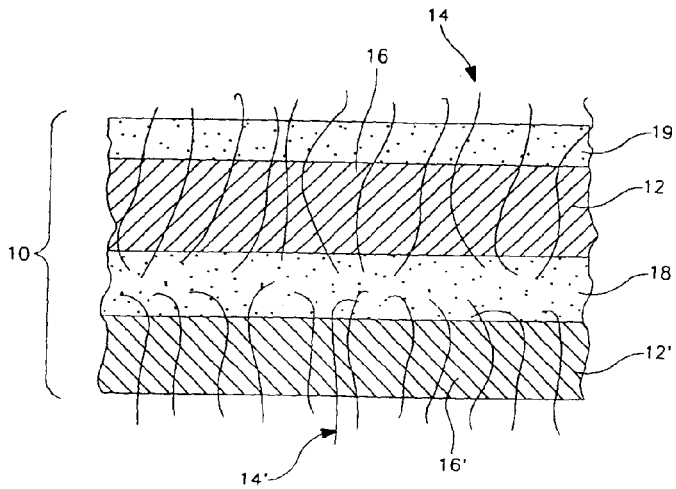

UNITED STATES PATENT AND TRADEMARK OFFICE
CERTIFICATE OF CORRECTION

PATENT NO. : 6,638,881 B2
DATED : October 28, 2003
INVENTOR(S) : Herbert Lapidus It is certified that error appears in the above-identified patent and that said Letters Patent is hereby corrected as shown below:

The title page should be deleted and substitute therefore the attached tilte page as shown on the attached page.

Drawings,
Delete drawing sheets 1-7 and substitute therefore the drawing sheets, consisting of Figs 1-7 as shown on the attached pages.

Signed and Sealed this

Twenty-first Day of September, 2004

JON W. DUDAS
*Director of the United States Patent and Trademark Office*

United States Patent
Lapidus

(10) Patent No.: US 6,638,881 B2
(45) Date of Patent: Oct. 28, 2003

(54) DENTAL ADHESIVE DEVICE AND METHOD OF PRODUCING SAME

(75) Inventor: Herbert Lapidus, Ridgefield, CT (US)

(73) Assignee: Combe Incorporated, White Plains, NY (US)

(*) Notice: Subject to any disclaimer, the term of this patent is extended or adjusted under 35 U.S.C. 154(b) by 255 days.

(21) Appl. No.: 09/747,805

(22) Filed: Dec. 22, 2000

(65) Prior Publication Data

US 2002/0006980 A1 Jan. 17, 2002

Related U.S. Application Data

(60) Provisional application No. 60/171,592, filed on Dec. 23, 1999.

(51) Int. Cl.$^7$ .............................................. B32B 27/12
(52) U.S. Cl. .................... 442/149; 442/151; 442/393; 442/394; 428/343; 156/278; 156/283
(58) Field of Search .................... 428/343; 442/394, 442/393, 149, 151; 156/278, 283

(56) References Cited

U.S. PATENT DOCUMENTS

| | | | |
|---|---|---|---|
| 2,897,593 A | 8/1959 | Hollander et al. | 32/2 |
| 2,978,812 A | 4/1961 | Rosenthal et al. | 32/2 |
| 3,575,915 A | 4/1971 | Novak et al. | 260/29.6 |
| 3,868,340 A | 2/1975 | Keegan et al. | 260/17.4 |
| 3,990,149 A | 11/1976 | Nedwig | 32/2 |
| 4,503,116 A | 3/1985 | Lapidus | 428/286 |
| 4,608,088 A | 8/1986 | Lokken | 106/35 |
| 4,632,880 A | 12/1986 | Lapidus | 428/523 |
| RE33,093 E | 10/1989 | Schiraldi et al. | 424/676 |
| 4,880,702 A | 11/1989 | Homan et al. | 428/354 |
| 5,166,233 A | 11/1992 | Kuroya et al. | 524/37 |
| 5,209,777 A | 5/1993 | Altwirth | 106/35 |
| 5,369,145 A | 11/1994 | Gasman et al. | 523/120 |
| 5,525,652 A | 6/1996 | Clarke et al. | 524/37 |
| 5,624,745 A | 4/1997 | Lapidus | 428/308.8 |
| 5,658,586 A | 8/1997 | Rajaiah et al. | 424/435 |

FOREIGN PATENT DOCUMENTS

| | | |
|---|---|---|
| EP | 0353375 | 8/1988 |
| EP | 0396411 | 11/1990 |
| JP | 63 54318 | 3/1988 |
| JP | 149110 | 5/1992 |
| JP | 65210 | 3/1993 |
| JP | 65211 | 3/1993 |

Primary Examiner—Elizabeth M. Cole
(74) Attorney, Agent, or Firm—Fitzpatrick, Cella, Harper & Scinto

(57) ABSTRACT

An improved dental adhesive device to hold prosthetic devices in the human mouth is made as a laminate of webs which are bonded together by deforming a film of thermoplastic ethylene oxide polymer and having an external adhesive coating on the laminate. The dental adhesive is produced by continuously applying thermoplastic ethylene oxide polymer between moving webs of cellulose acetate fibers, applying additional thermoplastic ethylene oxide polymer to the external surface of the webs, and then passing said webs in superimposed relationship between a pair of dry heated calender rolls for thermoplastically bonding said webs into a unitary structure. A dry water-activated adhesive material, such as sodium alginate, may be employed with the thermoplastic ethylene oxide polymer by being dissolved or dispersed in the polymer. Synthetic fibers are applied to the webs so as to extend transversely through the webs.

22 Claims, 7 Drawing Sheets